(12) United States Patent
Porter et al.

(10) Patent No.: US 6,823,717 B2
(45) Date of Patent: Nov. 30, 2004

(54) HYBRID MICROCANTILEVER SENSORS

(76) Inventors: Timothy L. Porter, 3001 N. Rio De Flag, Flagstaff, AZ (US) 86004; Michael P. Eastman, 3801 N. McColl St. #1120, McAllen, TX (US) 78501; Clay Macomber, 323 Rover Blvd., White Rock, NM (US) 87544

(*) Notice: Subject to any disclaimer, the term of this patent is extended or adjusted under 35 U.S.C. 154(b) by 0 days.

(21) Appl. No.: 10/454,344

(22) Filed: Jun. 3, 2003

(65) Prior Publication Data

US 2004/0194534 A1 Oct. 7, 2004

Related U.S. Application Data

(60) Provisional application No. 60/385,664, filed on Jun. 3, 2002.

(51) Int. Cl.[7] .............................................. G01N 7/00
(52) U.S. Cl. .................. 73/31.05; 73/29.05; 73/335.03
(58) Field of Search ............................. 73/24.01, 24.06, 73/31.05, 29.05, 31.01, 31.02, 31.03, 335.02, 335.03, 335.04, 335.05

(56) References Cited

U.S. PATENT DOCUMENTS

| | | | |
|---|---|---|---|
| 2,509,593 A | * | 5/1950 | Goddard ....................... 331/65 |
| 3,260,104 A | | 7/1966 | King, Jr. |
| 3,523,244 A | * | 8/1970 | Goodman et al. .......... 324/689 |
| 4,361,026 A | | 11/1982 | Muller et al. |
| 4,631,952 A | * | 12/1986 | Donaghey .................. 73/25.03 |
| 4,708,019 A | * | 11/1987 | Rubner et al. ................. 73/760 |
| 5,028,394 A | * | 7/1991 | Lowell et al. ................. 422/58 |
| 5,445,008 A | * | 8/1995 | Wachter et al. ............ 73/24.06 |
| 5,461,274 A | * | 10/1995 | Yuji et al. .................... 310/330 |
| 5,482,678 A | * | 1/1996 | Sittler .......................... 422/90 |
| 5,536,963 A | | 7/1996 | Polla |
| 5,679,888 A | * | 10/1997 | Tohda et al. .................. 73/105 |
| 5,698,931 A | * | 12/1997 | Shibata et al. .............. 310/338 |
| 5,719,324 A | | 2/1998 | Thundat et al. |
| 5,877,411 A | | 3/1999 | Namerikawa et al. |
| 5,955,659 A | | 9/1999 | Gupta et al. |
| 6,016,686 A | | 1/2000 | Thundat |
| 6,041,642 A | | 3/2000 | Duncan |
| 6,109,852 A | | 8/2000 | Shahinpoor et al. |
| 6,183,097 B1 | | 2/2001 | Saif et al. |
| 6,196,052 B1 | | 3/2001 | May et al. |
| 6,201,980 B1 | | 3/2001 | Darrow et al. |
| 6,287,765 B1 | | 9/2001 | Cubicciotti |
| 6,289,717 B1 | | 9/2001 | Thundat et al. |
| 6,303,288 B1 | * | 10/2001 | Furcht et al. ................... 435/4 |
| 6,447,887 B1 | | 9/2002 | Claus et al. |
| 6,475,750 B1 | | 11/2002 | Han et al. |
| 6,514,689 B2 | | 2/2003 | Han et al. |
| 6,523,392 B2 | * | 2/2003 | Porter et al. ............... 73/24.01 |
| 2003/0137216 A1 | | 7/2003 | Tamayo de Miguel et al. |

FOREIGN PATENT DOCUMENTS

JP          2000-214072 A       8/2000

OTHER PUBLICATIONS

PCT International Search Report dated Mar. 1, 2004, from corresponding International Application PCT/US03/17560 filed Jun. 3, 2003.

Ricco et al., "Chapter 23: Chemically Sensitive Interfaces on Surface Acoustic Wave Devices," *Interfacial Design and Chemical Sensing*, Washington D.C., 1994, pp. 264–279.

Baselt et al., "Biosensor Based on Force Microscope Technology," J. Vac. Sci. Technol., 1996, vol. 14(2), pp. 789–793.

(List continued on next page.)

*Primary Examiner*—Michael Cygan
(74) *Attorney, Agent, or Firm*—Christie Parker & Hale, LLP

(57) ABSTRACT

An apparatus and method for sensing chemical and/or biological analytes in a gaseous or liquid medium by monitoring the changes in impedance and thickness of a sensing element in the presence of the analyte is provided. Detecting means are provided to measure the change in the physical property of the sensing material to determine the presence and/or the amount of analyte present. An array of hybrid sensors dedicated to detecting a particular analyte which may be included in the medium, is also provided.

44 Claims, 26 Drawing Sheets

OTHER PUBLICATIONS

Eastman et al., "Application of the Solubility Parameter Concept to the Design of Chemiresistor Arrays," Journal of the Electrochemical Society, 1999, vol. 146, No. 10, pp. 3907–3913.

Fritz et al., "Translating Biomolecular Recognition into Nanomechanics," Science, Apr. 14, 2000, vol. 288, pp. 316–318.

Lonergan et al., "Array–Based Vapor Sensing Using Chemically Sensitive, Carbon Black–Polymer Resistors," Chem. Mater., 1996, vol. 8, pp. 2298–2312.

Lundberg et al., "Resistivity of a Composite Conducting Polymer as a Function of Temperature, Pressure, and Environment: Applications as a Pressure and Gas Concentration Transducer," J. Appl. Phys., 1986, vol. 60, No. 3, pp. 1074–1079.

Porter et al., "Polymer–Based Materials to be Used as the Active Element in Microsensors: A Scanning Force Microscopy Study," Journal of Scanning, 2000, vol. 22, pp. 1–5.

Porter et al., "Sensor Based on Piezoresistive Microcantilever Technology," Sensors and Actuators, 2001, vol. A88, pp. 47–51.

Ricco et al., "Chemically Sensitive Interfaces on Surface Acoustic Wave Devices," Interfacial Design and Chemical Sensing, Washington D.C., 1994, pp. 264–279.

Ruschau et al., "0–3 Ceramic/Polymer Composite Chemical Sensors," Sensors and Actuators, 1989, vol. 20, No. 3, pp. 269–275.

Talik et al., "Sensing Properties of the CB–PCV Composites for Chlorinated Hydrocarbon Vapours," J. Mater. Sci., 1992, vol. 27, pp. 6807–6810.

Thayson et al., "Polymer–based Stress Sensor with Integrated Readout," Journal of Physics D: Applied Physics, 2002, vol. 35(21), pp. 2698–2703.

Thundat et al., "Thermal and Ambient–induced Deflections of Scanning Force Microscope Cantilevers," J. Appl. Phys. Lett., 1994, vol. 64(21), pp. 2894–2896.

Wachter et al., "Micromechanical Sensors for Chemical and Physical Measurements," Rev. Sci. Instrum., 1995, vol. 66(6), pp. 3662–3667.

* cited by examiner

HYBRID MICROCANTILEVER SENSORS

CROSS-REFERENCE TO RELATED APPLICATION

This application claims priority of U.S. Provisional Application No. 60/385,664, filed Jun. 3, 2002.

STATEMENT REGARDING FEDERALLY SPONSORED RESEARCH

Financial assistance for this project was provided by U.S. Government Grant No. DMR-0071672, and the United States Government may own certain rights to this invention.

FIELD OF THE INVENTION

The present invention relates most generally to microsensors for sensing chemical or biological analytes, and, more particularly, the present invention is related to hybrid sensors capable of simultaneously measuring the thickness and conductivity change of a polymer film exposed to a particular chemical and/or biological analyte to sense the presence of particular chemical and/or biological analytes.

BACKGROUND OF THE INVENTION

The construction of rugged, inexpensive, reliable and small chemical microsensors whose output can be expressed in terms of a measurable electrical signal such as DC conductivity is of current interest. The goal of current research and development is to construct devices that can detect and identify chemical or biological analytes alone or in a complex mixture. Ideally, such sensors should be able to function in either a liquid or vapor environment.

Fields where the demand is great are volatile gas detection for environmental studies, medicine, and counterterrorism. Sensing of organic vapors has been achieved by measuring changes in conductivity or thickness of organic thin films. Specifically, volatile airborne organics when spilled or accidentally released into the air can have harmful effects on the internal operations of instruments and living creatures. Early detection can minimize damage and expedite cleanup procedures.

Identification and quantification of airborne organics such as benzene, tetrahydrofuran, ethanol, chloroform, and others has been demonstrated by Freund and Lewis (*Proceedings of the National Academy of Sciences,* 92, 2652 (1995)) using a polypyrrole material based 'organic nose' sensing unit. The sensor was formed by depositing a polypyrrole thin film on a cross sectional cut of a capacitor. The cross section had parallel rows of metal to which leads were attached to. The conductive polymer bridged the gap between the metal, completing the previously open circuit. The polymer was sensitive to the exposed airborne gases, absorbing them into the thin film. An array of these sensing elements produced a chemically reversible and consistent pattern of electrical resistance changes upon exposure to different organic analyte vapor. These patterns were repeatable and unique for each analyte.

Medically, the ability to detect biogenic amines would aid doctors in the diagnosis of disease. For example, biogenic amines such as aniline and o-toluidine have been reported as biomarkers for lung cancer, while di and tri-methylamines have been reported as the cause of the fishy uremic breath observed by patients with renal failure. Early detection of these amine groups would expedite diagnosis and treatment of patients. This technology could also allow for remote diagnosis by doctors of patients living in areas without proper health care Polyaniline polymer doped with carbon black has yielded a class of chemiresistor detectors able to sense amine groups at a sensitivity 1 million fold greater than that of the human olfactory system (G. Sotzing, et al., *Chem. Mater.,* 12, 593–595, (2000)). When an amine analyte such as butylamine is exposed to the film it causes a swelling in the polymer film. This swelling moves the conductive carbon atoms farther apart from each other within the film matrix. The film resistance increases due to the increased distance between the conductive carbon atoms. The resistance increase for the amine groups tested was unique and differentiable from the other responses.

Finally, in light of the emerging terrorism threat, the ability to detect nerve gases or other volatile/toxic gases in public buildings and transportation areas by reliable sensing equipment has become of increased importance. Polyethylene oxide polymer chemiresistors doped with lithium perchlorate have been shown to accurately detect and differentiate between the nerve gas simulants diisopropylmethylphosphonate (DIMP), dimethylformamide (DMMP), and dimethylmethylphosphonate (DMF) (R Hughes, et al., *Journal of The Electrochemical Society,* 148, 1–8, (2001)). In this system the polymer molecules rearrange during film swelling as the analyte is absorbed. The conductivity of the system increases because the mobile charge has more opened pathways to travel through The AC impedance of the system is reduced by a characteristic amount, producing a signature impedance change for each gas.

As early as 1986 the general principles behind chemiresistor detectors had been demonstrated. Early sensing experiments using metal ion doped phthalocyanine thin films spread on the surface of Interdigitated (IDA) electrodes showed resistance changes in the film when exposed to organic analyte vapor. These systems relied on the fact that the resistance for a given thin film depended upon the type of vapor (and its concentration) exposed to the sensor. Consistent resistance responses to gas exposure have been shown by organic polymer based systems doped with a conductive ion or plasticizer. Other materials such as clays have also been successfully used.

Organic polymer systems work through the process of analyte gases diffusing (dissolving or partitioning) into the matrix of the polymer film. This changes the conductivity of the polymer by swelling or contracting the film and changing either the distance between conductive atoms or the pathway taken by the mobile charge. The simplest systems use organic polymers that are naturally conductive such as polyacetylene Melanin. The conductivity of such systems can be enhanced through the addition of a plasticizer that acts as a dielectric material in the polymer matrix. This enhances the intermolecular capacitance just as a dielectric does in a parallel plate system. The polymers conductivity can also be increased through the addition of a doping agent such as a conductive salt or carbon black residue. These two materials increase the charge carrying ability of the polymer through different means. The addition of a conductive salt increases the number of mobile charge carriers in the film allowing current to more easily flow.

Among the systems receiving attention in this regard are carbon-black organic polymer composites which are deposited by spin or drop coating on interdigitated arrays. Inclusion of the carbon black component into the active sensor material is for the sole purpose of obtaining a measurable DC conductivity through the non-conductive active polymer material. The introduction of analyte material causes polymer swelling and consequent resistance changes of the polymer composite films. To identify specific vapors from a suite of possible substances and to determine the concentration of that vapor or to carry out similar measurements on multi-component systems requires the construction of arrays of sensing elements. Pattern recognition techniques or principal component analysis of the output of an array of sensors can be used for purposes of analyte identification and quantification.

In such systems carbon black acts as a conductive bridge between its atoms. The charge flows more easily when atoms are close together and has more difficulty flowing when the polymer swells and increases the carbon atom separation. Carbon black sensors have differentiated between things as closely related as molecular enantiomers. For example, in one system a chiral polymer was doped with carbon black and then exposed to the + and − forms of an enantiomeric gas. The gas was absorbed differently between the +/− case and a 10–20 Ohm difference in the total resistance response was observed between the two molecules (E. Severin et al., *Anal. Chem.* 70, 1440–1443, (1998)).

However, a number of shortcomings are associated with the use of the carbon-black organic polymer composites. First, it is difficult to reliably reproduce the performance characteristics of a given set of chemiresistor elements due to uncontrollable variations in composite construction. Second, spin coated or drop coated carbon-black polymer composites are inherently metastable in nature and may change or degrade with time. Third, metastable composite systems may not reliably adhere to a substrate surface. Fourth, repeated exposure of the metastable sensor element to analyte vapor may lead to misleading drifts and/or changes in performance characteristics. Fifth, the carbon in a composite material may slowly release analyte material following exposure to analyte and thus have a slow recovery time. Sixth, the interdigitated arrays generally consist of two components—a glass substrate and a metallic thin film or wire along with interface regions. Such complicated structures can lead to adhesion problems. Furthermore, carbon-black cannot be used for biological sensing because sensors based on biological molecules and attached to a substrate cannot effectively incorporate a material such as carbon-black.

Accordingly, a need exists for an enhanced microsensor that has improved sensitivity to identifying the presence of and quantifying the concentration of a particular analyte.

SUMMARY OF THE INVENTION

The present invention provides a method and apparatus for determining the presence and quantity of biological and/or chemical analytes using a hybrid sensor capable of simultaneous measurement of a volumetric and electrical property of a material responsive to the presence of the particular biological or chemical analyte of interest.

In one embodiment, the hybrid sensor according to the present invention analyzes a sample by simultaneously monitoring the impedance and thickness changes in a sensor material exposed to a sample.

In another embodiment, the sensor material is a lithium perchlorate doped polyethylene oxide thin film.

In still another embodiment, the impedance is measured by a frequency analyzer in signal communication with a sensing material and/or the thickness is measured by a deflectable microcantilever sensor in contact with a surface of the sensing material.

In yet another embodiment, the hybrid sensor is designed to determine both the identity and concentration of a particular analyte in a sample.

In still yet another embodiment, the invention is directed to a hybrid sensor system comprising an array of separate hybrid sensors.

In still yet another embodiment, the invention is directed to a method of constructing a hybrid sensor according to the current invention.

In still yet another embodiment, the invention is directed to a method of determining at least one of the identity and/or concentration of an analyte in a sample using a hybrid sensor as described herein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

The present invention is directed to a hybrid sensor capable of analyzing analyte vapors by simultaneously measuring changes in the thickness and the conductivity of an organic polymer or composite material thin film.

Figure 1:
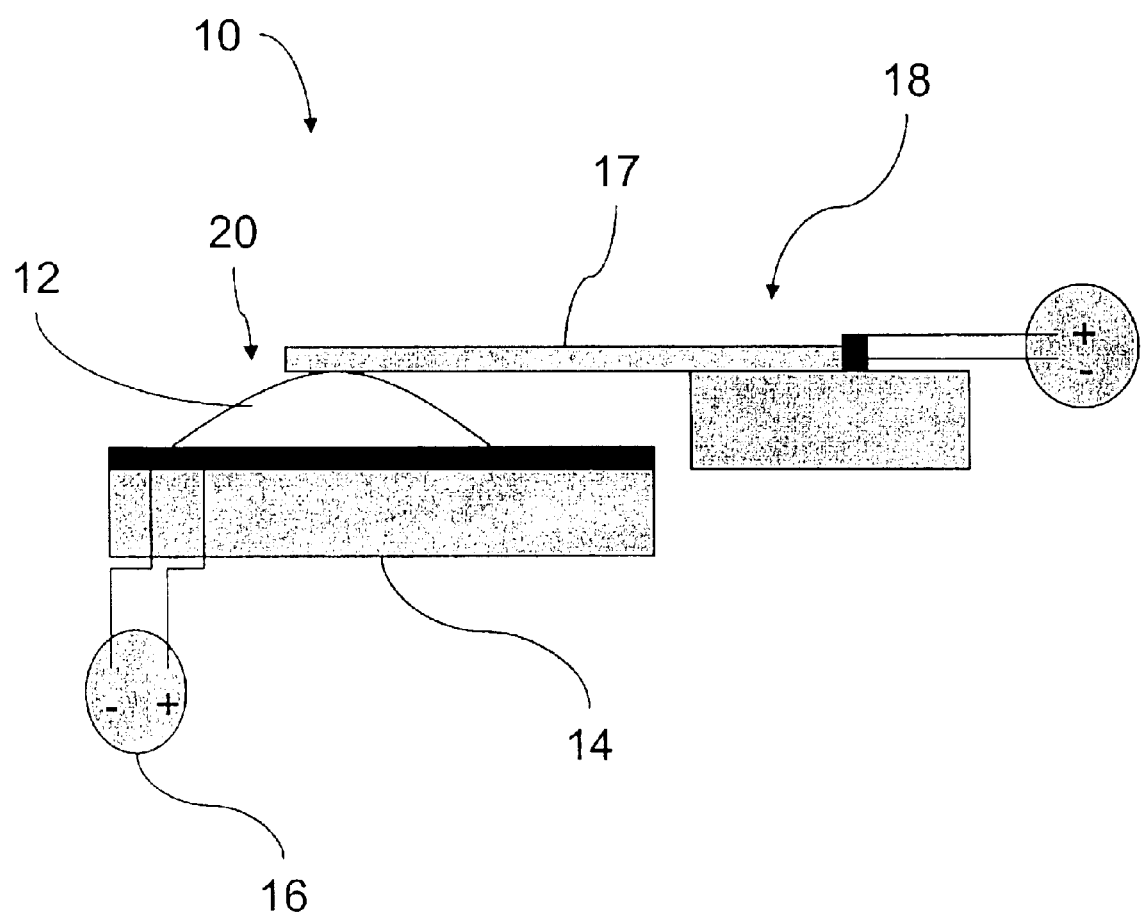
FIG. 1 is a schematic diagram of an exemplary embodiment of a hybrid sensor according to the present invention.

Prior to relating the details of the current invention, the following are abbreviations used in the current application:

DIMP—diisopropylmethylphosphonate
DMF—dimethylformamide
DMMP—dimethylmethylphosphonate
FRA—frequency response analyzer
GPIB—general purpose interface bus
IDA—interdigitated array
$LiClO_4$—lithium perchlorate
PEO—polyethylene oxide
PEVA—poly (ethylene vinyl acetate)
PIB—poly (iso-butylene)
PVA—poly (vinyl acetate)
USB—universal serial bus In one exemplary embodiment, a schematic diagram of which is provided in FIG. 1, the hybrid sensor 10 is constructed by placing a sensing material 12 on a substrate 14 either directly integrated with a signal analyzer device 16 or in signal communication with a signal analyzer device, and then placing a deflectable arm 17 of a piezoelectric microcantilever 18 in contact with a surface 20 of the sensing material 12.

In such an embodiment, the piezoelectric microcantilever 18 is used for the thickness measurements and a signal analyzer 16, such as a frequency response analyzer for the impedance measurements. During operation the thickness and impedance data are measured simultaneously, characterizing the response of the thin film to exposure to a particular gas or liquid sample. The impedance change in the polymer sensing film can then be correlated with the simultaneous measure of thickness change due to swelling resulting in a highly sensitive multi-variable "fingerprint" of a particular analyte in a sample. The change of each variable can then be quantified and used to differentiate between the type of analyte and the concentration of the analyte in the sample.

The sensing material may be a chemical sensor material such as a polymer or a biological sensor material such as a biomolecule or a composite of several materials. The sensing material may be formed in a discrete deposit in electrical communication with the conductivity sensor and on a portion of the microcantilever sensor, such as on the tip end of the deflectable arm of the microcantilever, or as a continuous coating of the sensing element may be formed over the surface such that a portion of the deflectable arm is embedded therein.

As discussed above, the present hybrid sensor simultaneously monitors the conductivity and thickness of a sensor material to obtain a "fingerprint" for a particular analyte. For example, in the system described above, preferably an alternating current (AC) is used to measure the impedance of the lithium salt-doped PEO system. In such an exemplary system, the impedance (Z) of the flow of an electric current in a thin film is the AC equivalent to the direct current (DC) resistance of the material, however, the path length is not a factor in AC impedance as it is in DC resistance. An AC detection circuit is also preferred because application of a DC to results in induced charge concentration, i.e. polarization of the medium. The use of AC relieves this polarization phenomenon because the signal is a sine wave that is constantly shifting direction, never allowing congregation or separation of charge in the medium The measured impedance is dependant upon the frequency of the applied wave through the medium or component, such that the impedance can be expressed in polar notation (r,θ) with r equaling the magnitude of the signal and θ equaling the phase shift of the voltage behind the current. The total impedance can also be expressed in rectangular coordinates (a, b) with the real (a) and imaginary (b) components given by the complex relationship:

$$R = a + bi \quad (1)$$

or the equation:

$$Z^* = Z' + jZ'' \quad (2)$$

where Z' is the real component (a), Z" is the imaginary component (b), and Z* is the total impedance.

The measurement of hybrid sensor systems in accordance with the current invention generally mimics electrical circuits composed of capacitors and resistors in series and parallel. The resistors mimic the slight amount of drift of the mobile charge that occurs along the inside or outside of the polymer matrix, and the capacitors mimic the behavior of the mobile charge as it moves through the organic substrate. The ease with which the mobile charge moves through the matrix is dependant upon the concentration of mobile ions and the number of sites available to which the mobile charge can move. The channels and sites used by the mobile charge open and close dependent upon the state of the substrate. Accordingly, combinations of resistors and capacitors in series and parallel may be used to compose "tank circuits" to model the response of polymer system to varied conditions to determine the appropriate frequency to apply for a given polymer system.

Figure 2:
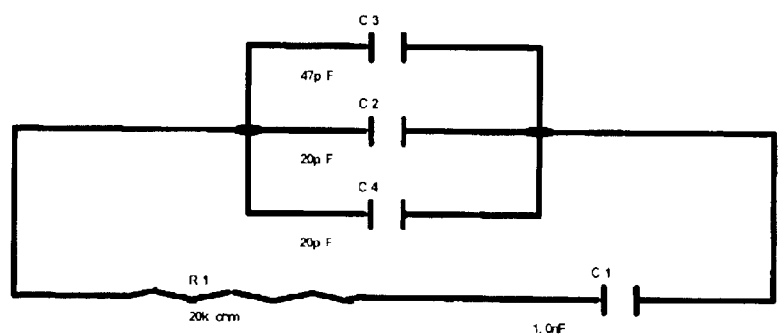
FIG. 2 is a schematic diagram of an exemplary embodiment of a "tank circuit" for modeling a hybrid sensor in accordance with the present invention.
Figure 3:
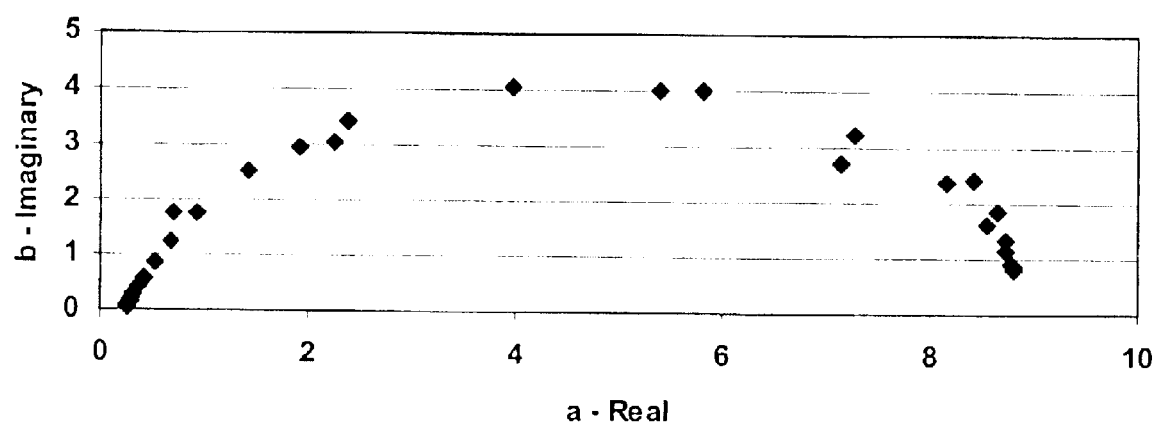
FIG. 3 is a Nyquist plot of some electrical properties of the "tank circuit" shown in FIG. 2.

One exemplary tank circuit for a system having multiple capacitors in parallel with a resistance is shown in FIG. 2 with its corresponding Nyquist plot shown in FIG. 3. As shown, in FIG. 3 when a frequency sweep is performed in on a parallel RC circuit of the type shown in FIG. 2, a semicircle is mapped. Indeed, multiple semicircles would be seen on the Nyquist plot if the frequency range were large enough. The point at the far right of the semicircle corresponds to the resistance of the circuit. The maximum peak of the semicircle is the point at which resistance and capacitance have an equal effect on the system. The point at the far left corresponds with an effective bypass of the capacitance due to the high frequency wave ignoring or bypassing the parallel plates.

Mathematical representations of sensor circuits can also be modeled from the basic definitions of impedance. These equations can then be used to calculate theoretical expectation values. With regards to the tank circuit shown in FIG. 2, the sum of the 3 capacitors ($C_2+C_3+C_4=C_p$) equals a capacitor in parallel to $R_1$ and $C_1$ and correlates to an impedance of $Z_1=-jx_1$. The resistive/capacitive components $R_1$ and $C_1$ are represented by $Z_2=R_1-jx_2$. The impedance Z's are in boldface because they are phasors. Phasors are vectors (having a magnitude and phase shift) associated with a harmonic function. Capacitances add in parallel as the sum of their individual capacitors. And impedances in parallel add as the sum of their reciprocals. The derivation follows according to:

$$\frac{1}{\tilde{Z}_1} = \frac{1}{\tilde{Z}_1} + \frac{1}{\tilde{Z}_2}$$

where:

$$\tilde{Z}_1 = -jx_1 \text{ and } \tilde{Z}_2 = R - jx_2$$

$$\tilde{Z}_1 = \frac{(-jx_1)(R - jx_2)}{-jx_1 + R - jx_2}$$

$$\tilde{Z}_1 = \frac{-x_1 x_2 - jx_1 R}{R - j(x_1 + x_2)}$$

$$Z_1 = \sqrt{\tilde{Z}\tilde{Z}'}$$

$$Z_1 = \sqrt{\frac{(x_1 x_2)^2 + (x_1 R)^2}{R^2 + (x_1 + x_2)^2}}$$

where:

$$x_1 = \frac{1}{2\pi f C_1} \text{ and } x_2 = \frac{1}{2\pi f C_p}$$

Figure 4:
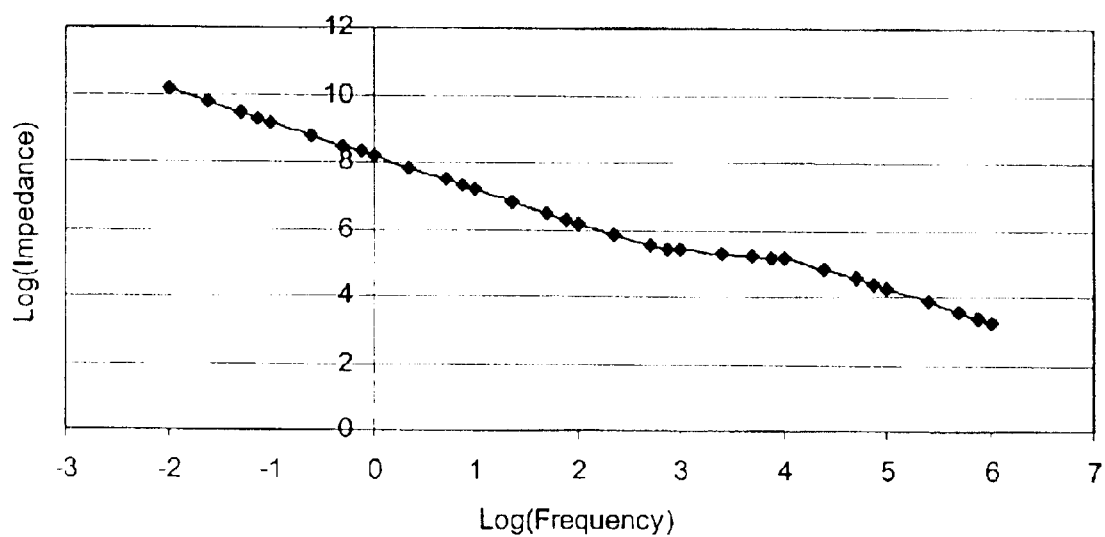
FIG. 4 is a plot of the impedance properties of the "tank circuit" shown in FIG. 2.

Using these equations expectation values can be calculated for the system in terms of (r, θ) where Z=r. Theoretical plots of these calculated impedance values for the model circuit shown in FIG. 2 are provide in the plot of FIG. 4.

Although the measurement of impedance can be carried out using a direct measurement circuit, as described above, the measurement of impedance in the hybrid sensors of the current invention can also be carried out indirectly using a frequency response analyzer (FRA). This generates an AC voltage (in the shape of a sine wave) applied across the sensor and a shunt resistor (the magnitude of which is similar to that of the sensor) in series. The instrument steps through the frequencies and analyses the voltage drop at each step across the sensor ($V_c$) and the shunt ($V_s$). The ratio of these two is displayed (along with the phase angle) and when this result is multiplied times the shunt resistor ($R_s$), the magnitude of the sensor impedance ($R_c=Z$) is known.

In such a system, the phase angle refers to the difference in phase between the sensor voltage and applied current. The total complex impedance can be plotted in a Nyquist plot (a,b), as a function of impedance vs. Log (frequency) (Z, Log (f)), or phase shift vs. Log (frequency) (θ, Log (f)). This method is described in detail in reference (P. Bruce, *Polymer Electrolyte Review*, "Electrical Measurements on Polymer Electrolytes" Elsevier Applied Science, London; New York, 1987 p. 266–269), the disclosure of which is incorporated herein by reference.

Figure 5:
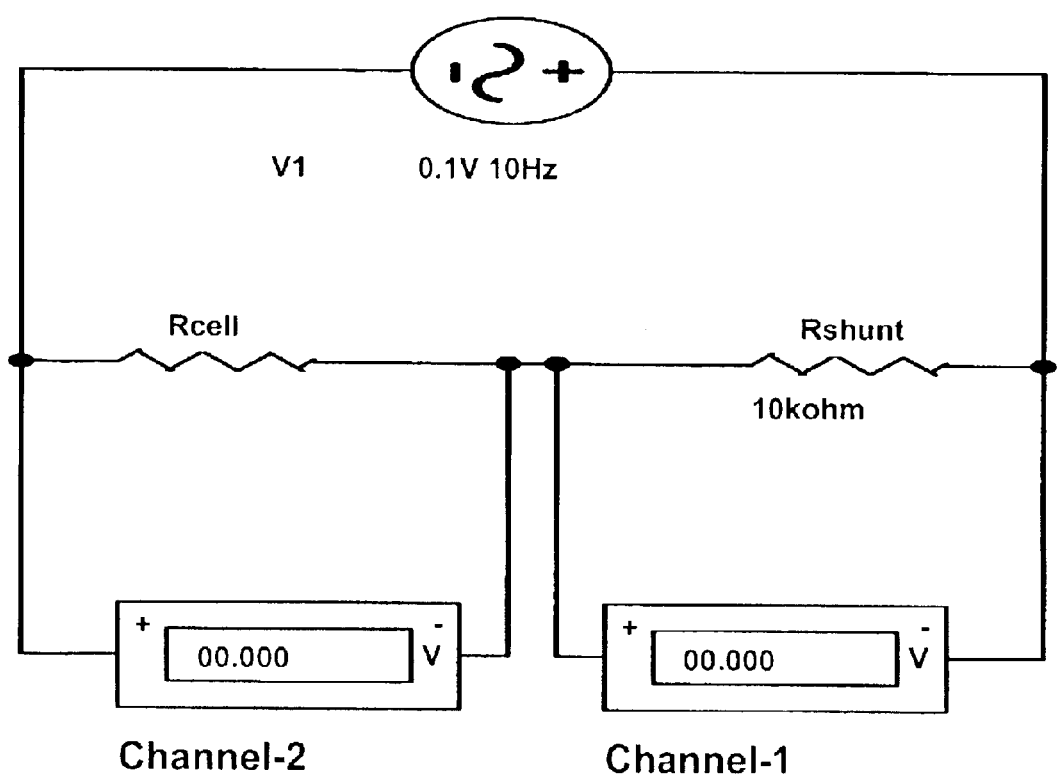
FIG. 5 is a diagram of an exemplary frequency response analyzer in accordance with the present invention.

Starting with the relationship V=I*R (R is effectively the magnitude of Z, without the phase shift) we can mathematically derive the relationship stated above, notice the current (I) is not present in the final expression. This is important because the current involved in these hybrid sensors are exceedingly small and difficult to measure without influencing its value. The amplitude of the voltage source can be modulated and in electrochemical systems a small voltage of 0.01V–0.1V is recommended to meet low power consumption requirements and to avoid damage to the system. A circuit diagram for one exemplary embodiment of an FRA for use in the current invention is provided in FIG. 5. The mathematical derivations for such an FRA are as follows:

$$V_s = IR_s \quad V_c = IR_c$$

$$\frac{V_c = IR_c}{V_s = IR_s}$$

-continued $$\frac{V_c}{V_s} = \frac{R_c}{R_s}$$

$$\frac{V_c}{V_s} * R_s = R_c \Rightarrow Z$$

In such a system, as previously discussed, impedance (Z) data can be returned by the machine in rectangular (a,b) or polar coordinates (r,θ) as previously discussed.

Because the impedance measurements of the sensors of the current invention are dependent on the frequency used to monitor the device, it is important to understand the frequency dependence of the sensors. For example, a sensor was constructed with a sensing material film consisted of a PEO: $LiClO_4$ mixture with a concentration ratio of 10:1 by weight, and a frequency sweep was performed on the sensor using an FRA. Sweep data for the sensor is shown in FIG. 6, wish phase shift data (originally collected as negative values) converted to positive degrees, following the convention of electrochemists.

Figure 7:
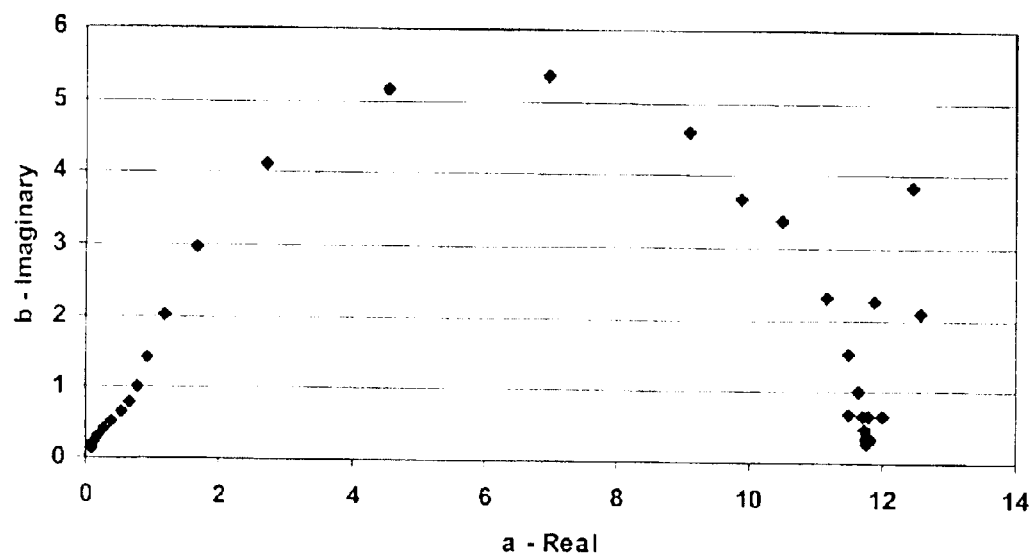
FIG. 7 is a Nyquist plot of an exemplary hybrid sensor in accordance with the present invention.

The rectangular coordinates were then converted to polar coordinates in accordance with the conversion equations described above, and the sensor data collected in polar coordinates was transferred to a Nyquist plot, as shown in FIG. 7. The semicircle observed corresponds with the model predicted earlier by the "tank circuit" modeling.

As discussed, each point represents a given frequency with low frequency values to the right and high frequency values to the left. The maximum value at the top of the semicircle occurs at a frequency of 178 Hz. This maximum value corresponds to the point were the contributions of the resistive and capacitive components are equal. The points that are purely resistive in nature occur at the extreme left and right of the plots. High frequency values fall on the left side, and have a value almost equaling zero, corresponding to the low resistance of the signal through the material. Low frequency values are found on the right side, which have the greatest resistance through the material.

Figure 6:
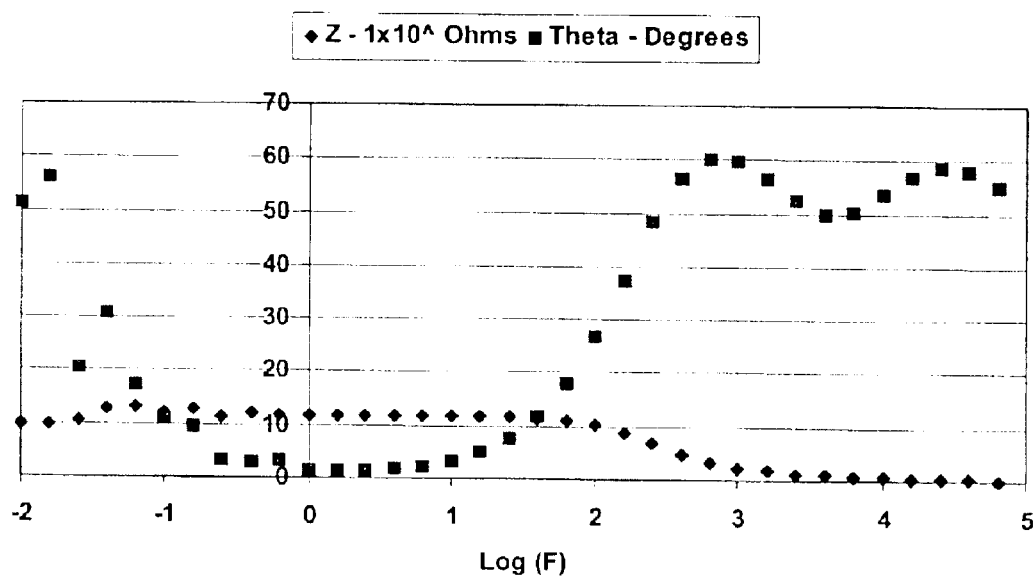
FIG. 6 is a plot of the impedance sensor of an exemplary hybrid sensor in accordance with the present invention.

Comparing the graphs in FIGS. 6 and 7 shows that the signal frequency of 10 Hz lies midway on the polar plot (at Log (F)=1) high impedance plateau, and on the Nyquist plot at the bottom of the semicircle on its far right side (~(12, 0.1)). This frequency has the largest resistance within the plateau region on the polar plot indicating that measurements taken at this frequency will yield measurements solely of the resistance of the sensor material.

Figure 8:
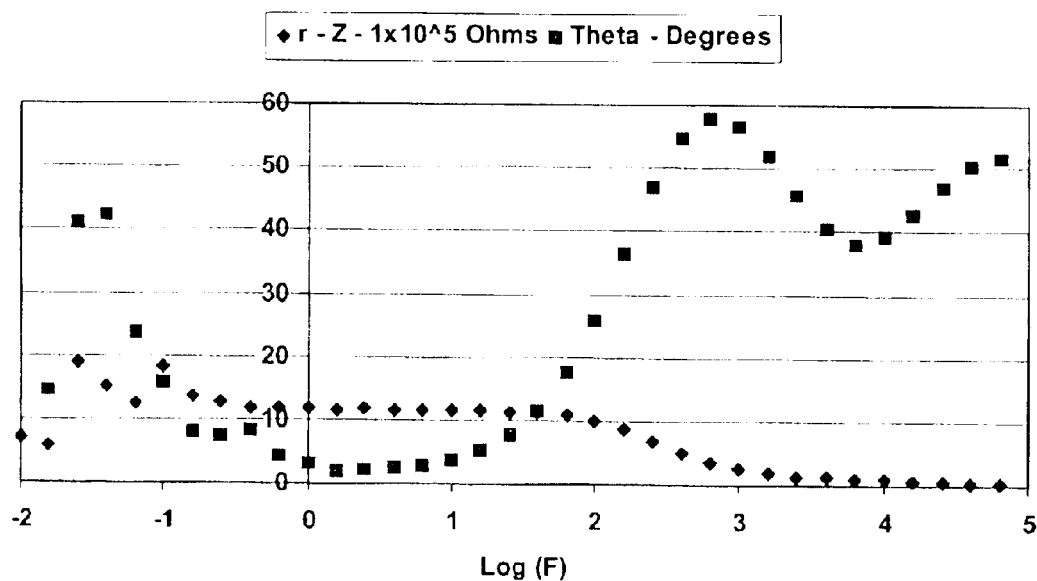
FIG. 8 is a plot of the impedance of an exemplary hybrid sensor in accordance with the present invention.
Figure 9:
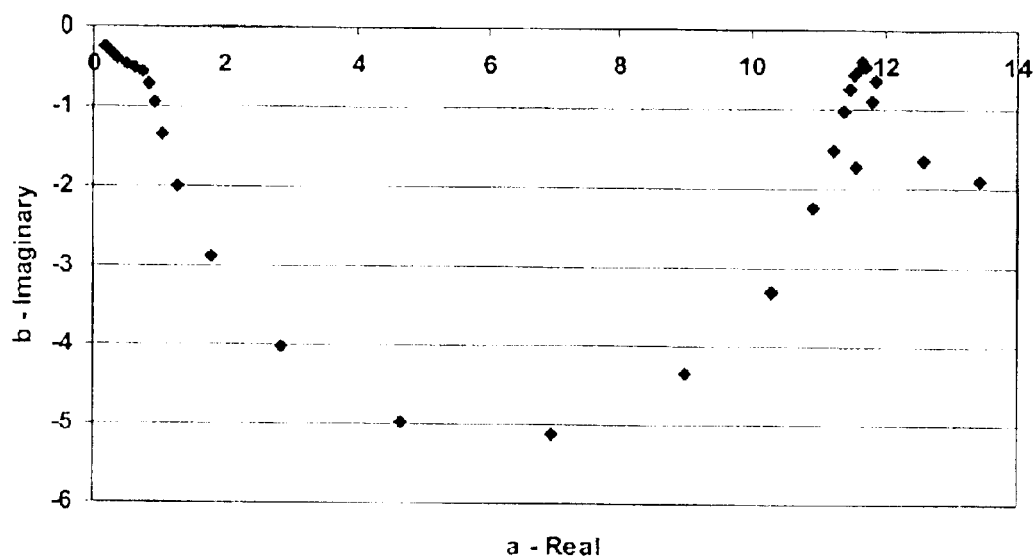
FIG. 9 is a Nyquist plot of an exemplary hybrid sensor in accordance with the present invention.

Frequency sweep data was also collected in rectangular coordinates and then converted to polar coordinates as shown in FIGS. 8 and 9. It should be noted that on the Nyquist plot the b values measured are negative, and all angle measures are converted to positives for the polar plot. Conversion of polar to rectangular coordinates and vice versa shows consistent results between each coordinate system. Again, the data corresponds to the previously shown tank circuit values and theoretical models with values on the order of $10.0 \times 10^5$ ohms in the low frequency range and $0.5 \times 10^5$ ohms in the high frequency range.

Although frequency sweep data for monitoring the impedance for one exemplary sensor was taken, it should be understood that such data could be obtained to determine the frequency dependence for any hybrid sensor system according to the present invention.

As discussed previously, in addition to determining the appropriate frequency for a particular measurement it is also important that the power consumption of sensing systems be kept as small as possible. Voltages that are too high use considerable power and can potentially damage the circuit through an electrochemical reaction, while voltages that are too low show an increased level of noise in measured data.

Figure 10:
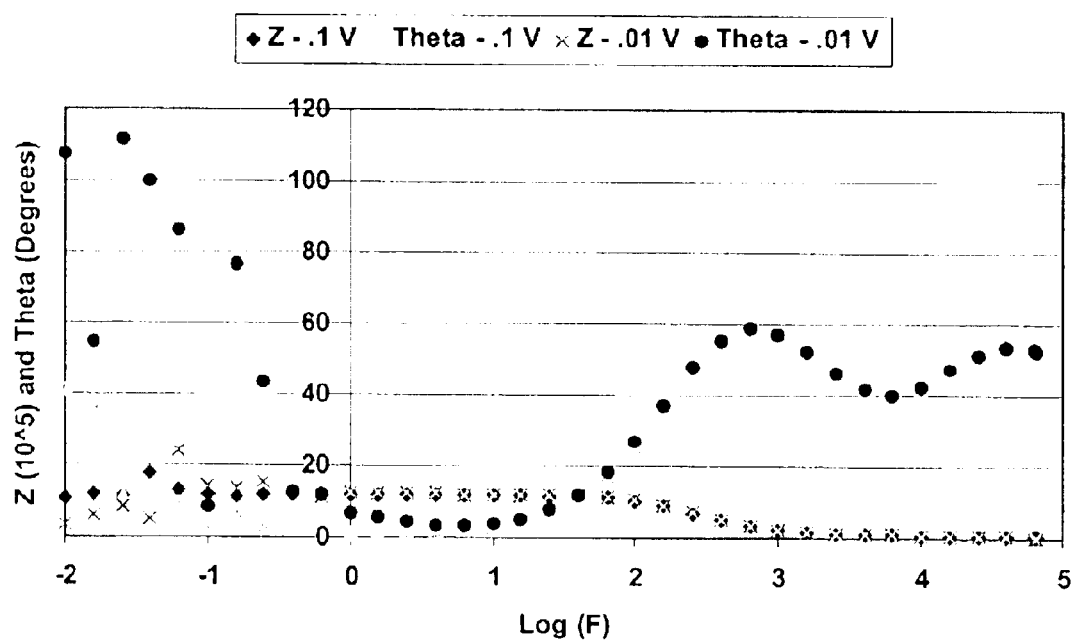
FIG. 10 is a plot of impedance versus voltage for an exemplary hybrid sensor in accordance with the present invention.

FIG. 10 shows a frequency sweep plot to determine the difference in noise in a sensor when different voltages are applied. In this plot frequency sweeps from 0.01 Hz to 65 kHz were performed on a sensor using a 0.01 Volt signal and 0.1 Volt signal to determine the noise difference between the two signals. As shown, in the mid and high frequencies there is no significant difference between either voltage signal. But, looking at the low frequency response we see large differences at the 0.01 Hz level until 10 Hz (log (F)=1) for the impedance and differences until 1 Hz (log (F)=0) for the phase shift. The 0.01 Volt signal is noisier and more erratic at these low frequency levels than the 0.1 Volt signal. The frequency of 10 Hz has been shown to give the greatest resistance response and this frequency lies at the edge of the noisy region for the 0.01 Volt signal. Accordingly, although certain frequencies will be more responsive to the resistance of the sensor system, it is also important to choose a frequency that is compatible with the voltage being used for the sensor.

Although specific frequency measurements are discussed above, it should be understood that such frequency sweep measurements of impedance can be used to both verify sensor operation and identify the ideal frequencies and voltages for impedance measurements in any suitable sensor.

For example, the values returned by the FRA on initial frequency sweeps of both the tank circuit and the exemplary sensors were on the order of $10 \times 10^5$ ohms at low frequency to $0.5 \times 10^5$ at high frequency. These values are on the same order of magnitude as the theoretically predicted values calculated above.

Moreover, using the frequency vs. time plots and Nyquist plots the identification of optimal measurement signals can also be determined. For example, in the measurements discussed above, the largest impedance measured was on the order of $10 \times 10^5$ ohms in the frequency range of 0.01 Hz to 100 Hz. The value of 10 Hz was identified as a promising frequency to use for signal measurement due to its position in the middle of this peak, and the lack of noise around the surrounding measurements. The signal frequency of 178 Hz was identified as another promising frequency because it occurred as the maximum value on the semicircular Nyquist plot. Although these values are preferred, it should be understood that less ideal values could be used to obtain impedance measurements for a hybrid sensor in accordance with the current invention.

The effect of voltage on noise in measurements was determined for 0.1 volts and 0.01 volts. Meeting the low power consumption requirements of microsensors mandates the use of a low voltage signal. It was determined that 0.1 volts would meet this requirement and the low noise constraint. For this voltage the noise present disappeared in frequency sweeps at 0.1 Hz while the 0.01 volt signal showed significant noise until 1 Hz, a power of 10 closer to the signal used for measurements of 10 Hz. From the combination of these measurements it was determined that one preferred embodiment of the hybrid sensors in accordance with the current invention would use frequencies of 10 Hz or 178 Hz and a voltage amplitude of 0.1 volts.

Although a frequency analyzer impedance sensor is described above, it should be understood that any signal analyzer capable of measuring the conductivity change in the sensor material may be utilized with the hybrid sensor of the current invention.

Meanwhile, the microcantilever sensor is formed on a substrate separate from the surface including the sensing material. Conventional semiconductor processing technology may be used to form the microcantilever. Various configurations and orientations of the microcantilever may be used. For example, in one embodiment, as shown, the microcantilever may include an overhang portion which extends over the edge of the microcantilever substrate and allows for the substrate and the surface containing the sensing material to be positioned in close proximity to one another such that the deflectable arm of the microcantilever may be at least partially attached and/or embedded within the sensing material. A micromanipulator such as the stage of a scanning tunneling microscope (STM) may be used to position and align the components.

The deflectable arm of the microcantilever will preferably be formed of semiconductor materials resistant to attack by analytes and the gaseous and liquid media which are introduced to the arrangement and which may include the targeted analyte. The deflectable arm is usable in both gaseous and liquid environments. The deflectable arm of the microcantilever includes at least one measurable physical property which changes when stress is created in the deflectable arm by the deflection of the embedded portion of the deflectable arm responsive to the volumetric change of the surrounding sensing material.

The dimensions of microcantilever portion of the hybrid detector including the deflectable arm will vary according to various embodiments. In one exemplary embodiment, the length of the deflectable arm may range from 100 microns to 200 microns, the height may range from 10 microns to 50 microns, and the width may range from 25 microns to 75 microns but other dimensions may be used alternatively. Furthermore, it should be noted that the essentially horizontal configuration of deflectable arm in its illustrated rest position is exemplary only and that deflectable arm may be formed tilted downward with respect to the horizontal when in its rest position. In that case, the axis of deflectable arm may form an acute angle with each of top and bottom of the substrate.

The materials of construction of the deflectable arm should be chosen such that the deflectable arm bends responsive to a volumetric change of the sensing material in the vertical direction, even if the deflectable arm is submerged within a liquid medium such as may be introduced to the sensing material for analysis.

The deflectable arm further includes at least one measurable physical property which changes when a stress is placed on the arm by the deflection of the arm in response to a vertical volumetric expansion of the surrounding sensing material as will be shown in subsequent figures. An example of a measurable physical property which changes when the deflectable arm deflects, is resistance. To provide a resistance which changes when the deflectable arm deflects, a piezoresistive member is formed within the deflectable arm. According to other exemplary embodiments, the piezoresistive member may be formed on the top surface or the underside of the deflectable arm.

According to an exemplary embodiment, the piezoresistive member may be a film such as barium titanate formed integrally within the deflectable arm during the microcantilever fabrication process. When the deflectable arm bends, the resistance of the piezoresistive member changes due to the mechanical strain in the member. The non-strained resistance of the microcantilevers may be on the order of 2 k ohms according to an exemplary embodiment. This exemplary measurable physical property therefore changes due to bending. Detecting means are used to measure this change in resistance. The microcantilever's sensitivity and the detecting means precision is such that bending of only a few tens of angstroms will result in a measurable resistance change.

To measure the change in resistance according to one exemplary embodiment, conductive wires may be coupled to the piezoresistive member through contacts. In such an embodiment, each of the contacts would extend through the top surface of the deflectable arm to contact the piezoresistive member. The conductive wires can then be coupled to a conventional electric circuit capable of measuring the resistance of piezoresistive member.

It should be understood that resistance as the measurable physical property of piezoresistivity is intended to be exemplary only. According to other exemplary embodiments, various other physical properties which change when the deflectable arm bends may also be used in conjunction with associated detecting means capable of measuring this change. According to a preferred embodiment, the detecting means is capable of measuring the extent of deflection. An electric circuit or other means may in turn be provided to facilitate measurement of the change in the measurable physical property. When measuring the change, the measurable physical property is preferably measured prior to and after bending, and the results compared to detect a change and the degree of change. The change itself can then be associated with the presence of the analyte sought to be detected, and the degree of change in the physical property will preferably correspond to the degree of arm deflection which, in turn, will preferably correspond to the amount or concentration of the analyte present. According to another exemplary embodiment, the deflectable arm may include more than one measurable physical property which changes when the arm deflects.

The present invention also provides detecting means such as various electric circuits which detect the change in the measurable physical property or properties of the deflectable arm. The measurable physical property will preferably be measured prior to and after the introduction of the medium which may include the analyte sought to be detected. The medium is introduced to intimately contact the sensing material.

The sensing material may be formed on the surface using conventional methods. For the illustrated exemplary embodiment in which the sensing material is formed as a discrete pad of material formed on the surface in signal communication with the impedance analyzer and partially encasing the overhang portion of the deflectable arm, the sensing material may be formed by drop deposition, such as by using microcapillaries, or using ink jet printer technologies to form a droplet directly atop the overhang portion of the deflectable arm. Other methods for depositing the sensing material may be used alternatively. Sensing material deposits may take on the shape of a puddle, pad or droplet. Alternatively, the surface or a portion of the deflectable arm itself may be derivatized prior to deposition of the sensing material, to promote adhesion.

As discussed above, any suitable sensing material may be used in the hybrid sensor of the current invention. In determining the suitability of a material for use as a sensing material in the current invention, the solubility parameter ($\delta$) provides a key to examining the type and number of polymer thin films needed to sense all possible airborne solvents. The solubility parameter is a measure of attractive strength or cohesive energy of the molecules in a material and was originally used to calculate the free energy of mixing fluids. This concept has been extended to solvents (gas or liquid) and polymers because solvents with approximately the same δ as a given polymer have a nearly zero enthalpy of mixing, consequently mixing spontaneously. Eastman and Hughes showed that poly (iso-butylene) (PIB) had a maximum sensitivity to analytes with a small δ value, while poly(vinyl acetate) (PVA) responded best to solvents with a large δ value (Eastman et al., *Journal of the Electrochemical Society*, 146, 3907–3913 (1999)). Using this parameter a universal sensor array can be theoretically proposed for a given solvent space. The number and type of polymers used would be pre-selected on the basis of their solubility parameter to cover the high, low, and intermediate values of the solvent space defined.

TABLE 1

Hildebrand Solubility Parameters for Common Solvents

| Solvent | Solubility Parameter ($\delta$, $Mpa^{1/2}$) | Partition coefficient water/octanol log P (calc.) | Saturation vapor pressure $P_{sat}$ at 23° C. (Torr) |
|---|---|---|---|
| Isooctane | 14.1 | 4.46 | 45 |
| Cyclohexane | 16.7 | 3.39 | 89 |
| 1, 11-Trichloroethane | 17.5 | 2.1 | 117 |
| Carbon tetrachloride | 17.7 | 2.86 | 100 |
| m-Xylene | 18 | 3.14 | 7 |
| Toluene | 18.2 | 2.68 | 26 |
| Benzene | 18.7 | 2.22 | 83 |
| Chloroform | 18.9 | 1.76 | 178 |
| Methyl ethyl ketone | 19 | 0.37 | 90 |
| Tetrahydrofuran | 19.5 | 0.33 | 160 |
| Chlorobenzene | 19.5 | 2.81 | 10 |
| Chlorohexanone | 19.6 | 0.76 | 4 |
| Benzaldehyde | 19.7 | 1.64 | 0.8 |
| DIMP | 20 | 0.9 | 0.7 |
| Tetrachloroethane | 20 | 2.17 | 12 |
| Acetaldehyde | 20.1 | −0.16 | 890 |
| 1, 1, 2-Trichloroethane | 20.2 | 1.68 | 22 |
| Trichloroethane | 20.2 | 2.26 | 68 |
| Acetone | 20.5 | −0.16 | 212 |
| Pyridine | 21.8 | 0.73 | 18 |
| DMMP | 22 | −0.86 | 3 |
| Cresol | 22.7 | 1.94 | 0.1 |
| Polyethylene oxide | 24.2 | | |
| N, N-dimethylformamide | 24.9 | −1.01 | 3.3 |
| Ethanol | 26 | −0.2 | 52 |
| Methanol | 29.3 | −0.72 | 114 |
| Water | 48 | −1.38 | 21 |

The sensing material may be sensitive to chemicals or biological materials. For the case of a chemical sensing material, pure polymers or composite materials of combination of polymers can be used to detect either liquid or vapor phase analytes. After formation, the polymeric sensing materials exhibit a somewhat rubbery consistency in an exemplary embodiment. The polymeric chemical sensing material is chosen to undergo volumetric expansion or contraction in the presence of at least one analyte sought to be detected. This occurs as the analyte is attracted to and combines with the sensing material, typically by adsorption, absorption, partitioning, or binding. Exemplary polymeric chemical sensor materials include poly(vinyl acetate) (PVA), poly(isobutylene) (PIB), poly(ethylene vinyl acetate) (PEVA), poly(4-vinylphenol), poly(styrene-co-allyl alcohol), poly(methylstyrene), poly(N-vinylpyrrolidone), poly(styrene), poly(sulfone), poly(methyl methacrylate), and poly(ethylene oxide) (PEO).

According to another exemplary embodiment, the polymeric chemical sensing material may be a composite material including more than one of the above or other exemplary compounds. Other sensing materials may be used alternatively. Upon exposure to the targeted analyte, the chemical sensor undergoes a volumetric change including in a vertical direction to place a stress on the deflectable arm in a vertical direction when the analyte is adsorbed by the sensing material.

The sensing material may also be a biological sensor such as a biomolecule, which undergoes a conformational change in the presence of the analyte sought to be detected. According to one exemplary embodiment, the sensing material may be a thiolated single strand DNA (deoxyribonucleic acid) attached to a substrate which may be formed of gold. The thiolated end of the DNA single strand adheres well to gold. Such a biological sensor can be used to detect the complementary DNA strand. DNA preferably exists in a double strand configuration. If the complementary DNA strand (the analyte) is included within the medium introduced to the sensing element, the complementary strand would strongly bind to the thiolated strand effectively increasing the thickness of the DNA layer on the gold substrate or, stated alternatively, produce a volumetric expansion in the vertical direction.

According to another exemplary embodiment of a biological sensor, a layer of antibodies, specific to the desired analyte to be sensed such as a particular virus, is formed over the surface. When the aralyte virus is present, it is strongly attracted to and subsequently binds to the antibody layer. In this manner, the layer thickness increases and represents a volumetric change in the vertical direction. According to other exemplary embodiments, other biological sensing elements may be used which undergo a physical or morphological change in response to the presence of the analyte sought to be sensed. In each case, the sensing material adsorbs the analyte and expands or contracts volumetrically in the vertical direction deflecting the embedded portion of the deflectable arm and creating a measurable stress on the portion of the deflectable arm attached to the base. According to yet another exemplary embodiment, the biological sensor may be chosen to volumetrically contract in the vertical direction in response to the presence of the analyte sought to be detected.

Figure 11A:
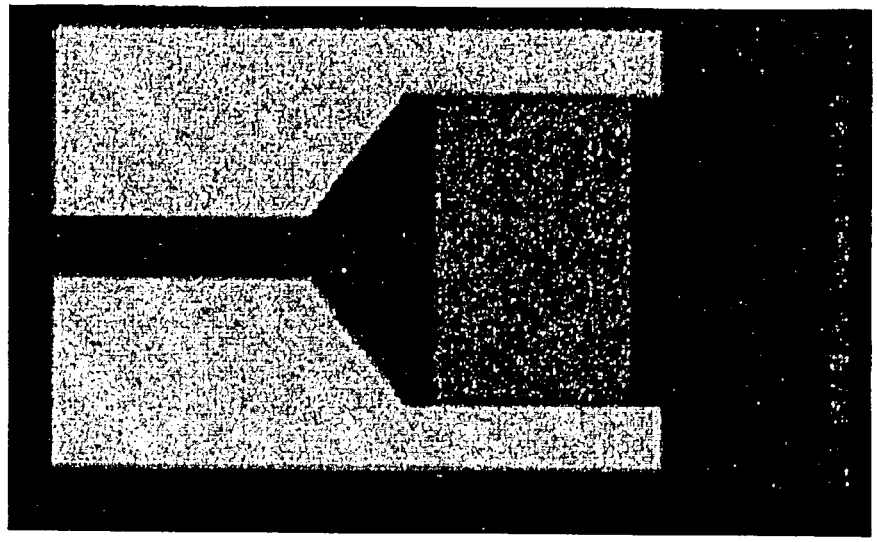
FIGS. 11a and 11b are photographs of exemplary interdigitated arrays in accordance with the present invention.
Figure 11B:
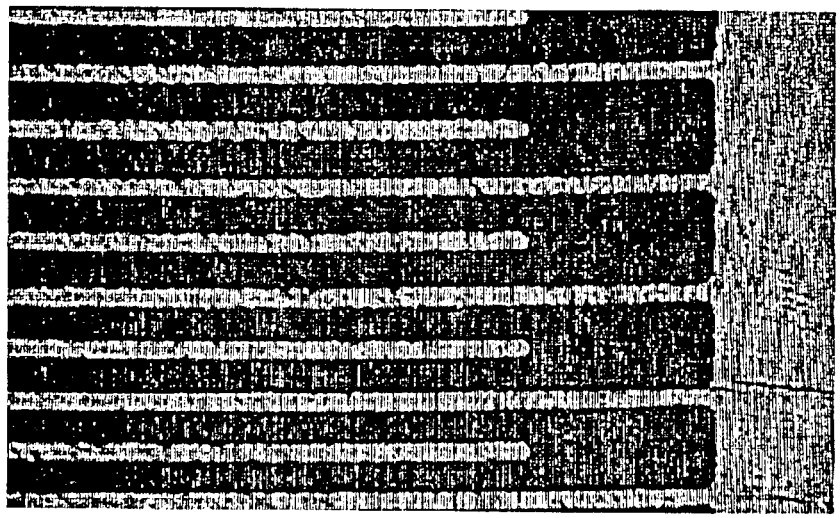

In one exemplary embodiment, the sensing material comprises a lithium perchlorate doped polyethylene oxide (PEO) thin film on an interdigitated array (IDA), such as that shown in either one of exemplary micrographs provided in FIGS. 11a and 11b. PEO is a particularly preferred polymer to use as a thin film sensing material because when PEO is doped with lithium salts the result is improved room temperature conductivity.

Although not to be bound by theory, the conductivity changes in a PEO material are believed to be related to the lithium ions ability to move through a PEO matrix. In such an embodiment, the response of the PEO polymer film will be characteristic of individual gases and will act as a 'fingerprint', which can be stored in a library and referenced later for Identification of unknown vapors. Aside from the conductivity of the polymer, other benefits of using PEO as a substrate include its durability over time and its ability to 'reset' itself to a baseline state after exposure to analyte vapor stops. PEO also shows good thermal durability, significant impedance response to varied volatile organic compounds, and reasonably rapid and complete resetability after exposure. Also, relatively small amounts of the polymer are needed to produce sensitive results.

Figure 12:
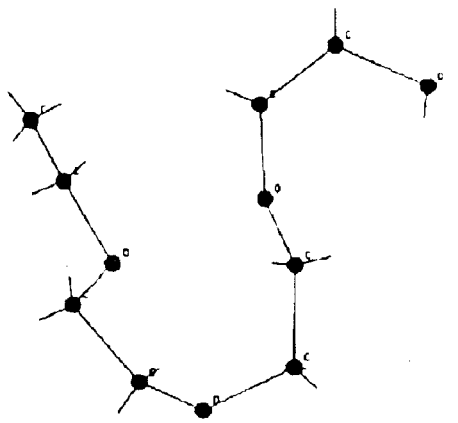
FIG. 12 is a schematic molecular diagram of the "hopping" phenomenon in lithium doped polyethylene oxide.
Figure 12:
Figure 12:
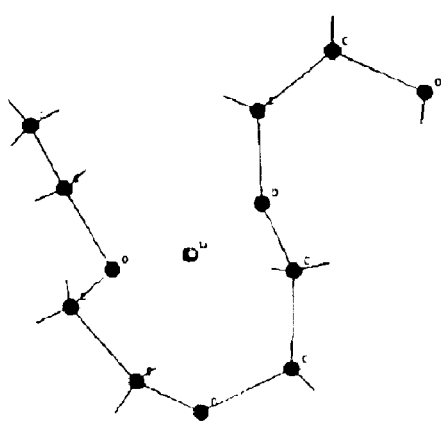
Figure 13A:
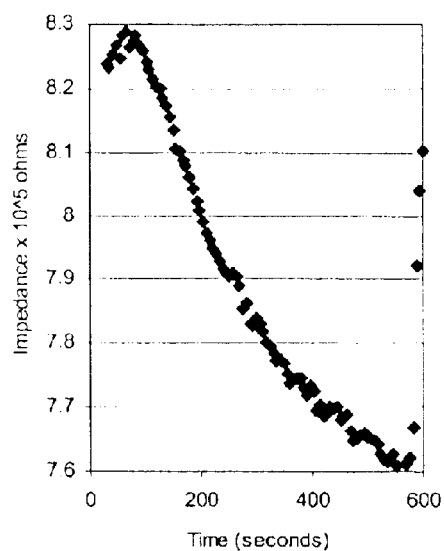
FIGS. 13a and 13b are plots of the impedance response of a hybrid sensor in accordance with the current invention when exposed to 100% water vapor.
Figure 13B:
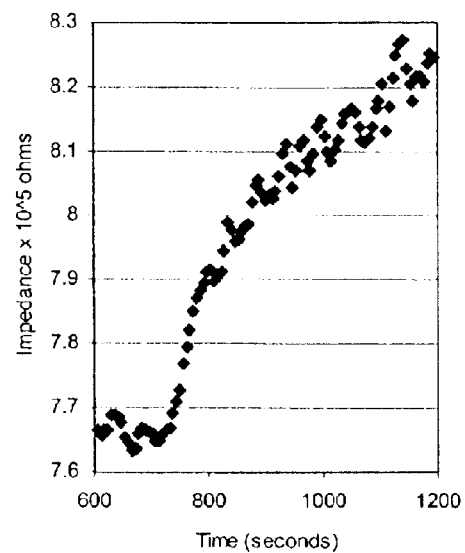
Figure 14A:
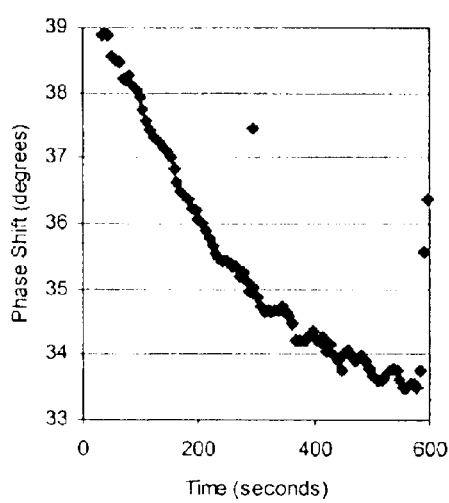
FIGS. 14a and 14b are plots of the phase shift response of a hybrid sensor in accordance with the current invention when exposed to 100% water vapor.
Figure 14B:
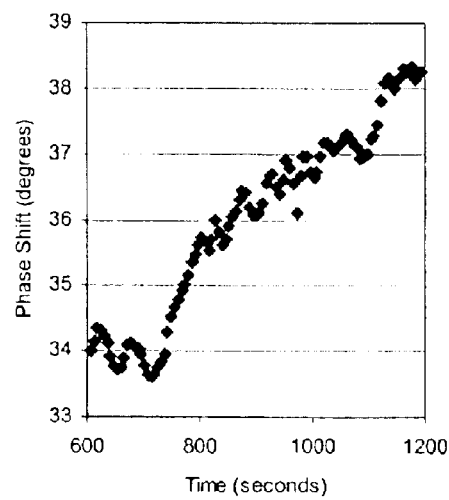

As previously discussed, PEG has a solubility parameter value of 24.2 $Mpa^{1/2}$, which is in the middle of Table 1, and corresponds to a number of organic analytes. Ethanol (26.0 $Mpa^{1/2}$) and Acetone (20.5 $Mpa^{1/2}$) fall on either side of PEO in the table and should mix easily. While isooctane (14.1 Mpa$^{1/2}$) and water (48 Mpa$^{1/2}$) lie far away from PEG at the extreme ends and should not mix well. However, when PEO is doped with lithium perchlorate the room temperature conductivity increases because when allowed to dry PEO forms long helical or zigzag conformations providing an environment where the Li cation has mobility within the polymer matrix. The positive mobile charge can move along the PEO molecules to different regions of negativity in a process called 'hopping', shown diagrammatically in FIG. 12.

Although not to be bound by theory, it is believed that the conductivity of the PEG thin film is related to the resistance in the flow of Li+ cations within the film matrix. Accordingly, during operation, analyte gas molecules enter the intergallery regions of the polymer matrix, rearranging the bottleneck resistances to charge flow allowing more or less room for the mobile charges to move. This action changes the AC impedance (of which DC resistance is a component) producing a signature resistance change for a given analyte. The unique resistance change is due to the physical and chemical characteristics of the analyte gas. The differences in size and polarization of the gas affect how much and how fast it will be absorbed into the polymer thin film.

Although any suitable ratio of PEO to Li+ may be used in the present invention, a preferred range of PEO:Li+ ratio lies in the region between 6:1 to 15:1 by weight. PEO:Li+ ratios within such a range have been found to yield actively conducting films. Lower concentrations of Li+ generally do not provide enough charge carriers moving freely about the system to increase conductivity, and using higher concentrations of Li+ (for example, as the mixtures get close to 1:1 by weight) and the polymer films will not dry to form a film but will maintain a tacky oily state.

Although PEO systems are discussed above, it should be understood that other pure polymer and doped polymer systems may be used in the current invention For example, the 'hopping' or 'tunneling' of mobile Li+ along channels in between negative regions in the polymer matrix has also been observed in polyaniline-polyethylene oxide systems.

EXAMPLES

A series of exemplary sensing studies were conducted on an embodiment of a sensor in accordance with the present invention. In the following studies a variety of chemicals were used for the sensor and imaging studies performed. The organic polymer used in the preparation of the thin film sensing material was Polyethylene oxide of molecular weight 4,000,000 g/mole purchased from Aldrich Chemical. The PEO was doped with Lithium Perchlorate (Baker Analytical, LiClO$_4$) to increase conductivity. Both PEO and LiClO$_4$ were dissolved in the polar aprotic solvent acetonitrile (Aldrich, CH$_3$CN). The sensor systems consisted of thin films of organic polymer spread onto interdigitated arrays (IDA) fabricated by Microsensor Systems. Wire leads were attached to the IDA using two types of conductive epoxy purchased from Ablestik and Loctite. Curing time of Ablebond (84-1LMISR4) was 2 hours in a 175° C. oven or overnight at room temperature for the Loctite 3888 epoxy. The IDA's were mounted to iron slugs using Elmer's rubber cement. Compressed nitrogen air tanks used in a bubbler apparatus were used as a carrier gas.

Impedance and phase shift data were acquired using a Solartron/Schlumberger 1250 Frequency Response Analyzer (FRA), which generates a frequency modulated signal that is recovered and analyzed after passing through the circuit cell. Thickness changes were measured using a piezoelectric cantilever purchased from Microscopes Inc. model #PLCT-SAMT. The bending of the cantilever produced a resistance response measured using a Keithley Multimeter 199 DMM. A portable hand held Wavetek X15 multimeter was employed for all other electrical troubleshooting. LabView graphical programming software along with a general purpose interface bus (GPIB/USB) plug from National Instruments was used to interface the FRA and Multimeter with a Sony (900 MHz Athlon processor/40 GB memory) microcomputer for data collection and monitoring purposes. Imaging and cantilever mounting was done with a Park Scientific Scanning Force Microscope (SFM). Thin Films were spread to uniformity by an adjustable film spreader built by Mitutoyo. The varying gas concentrations were delivered using a glass and Tygon tubing bubbler system connecting the dry nitrogen tank and the analyte bubbler tank to a head cap fitted for the SFM enclosing the hybrid sensor system.

SFM imaging was performed on the polymer film surfaces using topographical (showing surface features) and phase contrast (showing differences in material composition) settings. Scans were done at the 5 micron and 2 micron levels. The polymer was prepared as above, and the thin films were made by drip coating iron slugs with the polymer and spreading it to flatness using the film spreader. Images were taken of pure PEO polymer, of PEO doped with Li+ at 7:1, 10:1, 15:1, and 20:1 concentrations by weight, and at 25, 50, 75, and 100% water vapor.

Fabrication of the sensing unit started with a preliminary check of the IDA's. Using the pinpoint probes attached to a multimeter the resistance was measured at the electrode pads. The value returned should be infinite when none of the digits in the array touch neighboring digits. The surface of the IDA was visually inspected for cleanliness and any dirt or dust was removed with compressed air. Later acetonitrile was used to was the surface and increase adhesiveness of thin film. The sensor wiring was stripped of its insulation at the ends using nitric acid. The exposed wire was then cleaned with distilled water and chemwipes. Wiring resistance was measured and any wires with large resistances were discarded. A glass slide was used as a foundation to tape the IDA and wire leads down for fastening. The conductive epoxy was applied and allowed to cure in the oven or at room temperature. After the epoxy hardened the resulting connection was checked by measuring the resistance across the joint, by placing leads on the wire and gold pad with the epoxied region in the middle. A high (or infinite) reading corresponds to a bad (open circuit) connection.

PEO doped with LiClO$_4$ in a 10:1 ratio (by weight) was used as the organic thin film sensing material. Approximately 0.200 grams of PEO powder and 0.020 grams of LiClO$_4$ salt were placed in pre-weighed 10 ml beakers. Acetonitrile, 5 ml was pipetted into the beaker of LiClO$_4$. A magnetic stir bar was placed in the solution and the beaker was placed on a magnetic stir plate. The solid was stirred for 5 minutes at which time the LiClO$_4$ was completely dissolved. At this time the PEO powder was added to the lithium solution. After this addition, the PEO beaker was post weighed and an additional 4 ml of acetonitrile was added to the mixture. A clean #4 green stopper was placed on top of the beaker and the mixture was allowed to stir overnight. The stopper seals the container and prevents the solvent from evaporating. The result is a cloudy gel that was drip cast onto the IDA surface. The film was allowed to dry overnight before the IDA was mounted onto an iron slug using rubber cement. The sensor leads were then soldered to a coaxial conversion fence for attachment to the rear coaxial plugs of the FRA.

During measurement, baseline measurements of impedance (Z) and phase shift (θ) are taken by doing a logarithmic sweep of frequencies from 0.01 Hz to 65 kHz to insure proper operation of FRA and sensor impedance. For the thickness measurements the piezoelectric cantilever was lowered onto the surface of the film until a 1–3 ohm jump in the baseline resistance was observed. The bend is preloaded in the cantilever to keep from losing contact with the film surface during film contraction phases.

After the initial set-up and checks, the impedance and thickness components of the sensor are ready for gas exposure. At this time the gas lines were turned on and the head cap was placed over the sensor. The $N_2$ carrier gas was run through the bubbler apparatus where it picked up the analyte gas to be tested. Analytes tested included distilled water, ethanol 190 proof (Aldrich, $C_2H_5OH$), ethanol 200 proof (Aldrich), acetone (Aldrich, $CH_3COCH_3$), and n-octane (Lancaster, $C_8H_{18}$). The concentration of analyte gas delivered was adjusted from 0–100% using the bubbler controls and indicators. The sensor was exposed to dry $N_2$ for 15 minutes to reset the sensor before introduction of analyte vapor. The typical exposure cycle consisted of a thirty second baseline reading taken before the addition of analyte vapor until saturation of the thin film occurred. This was followed by dry $N_2$ again until a level baseline was achieved when all of the analyte had left the polymer. The thickness change due to the polymer exposure to vapor was monitored by the resistance response data taken by the cantilever. The FRA measured the impedance change with the generator set at 0.1 Volts and 10 Hz unless otherwise noted. The data was transferred to a spreadsheet and correlated graphically and mathematically.

Example 1

In a first exemplary embodiment, impedance measurements were taken using an IDA sensor coated with a thin film organic polymer sensing material connected to an FRA, as described above. Measurements were either stored into the FRA file memory or downloaded to the computer using a GPIB/LabView interface to the computer. Impedance change and phase shift were then measured as a function of time during exposure of 100% water vapor carried by $N_2$ gas to the sensor. The test was broken up into two parts with 99 data points taken as the thin film swelled and 99 taken as it relaxed. In part one the sensor was exposed to 100% water vapor from 0–530 seconds. The head cap was taken off from 530–600 seconds. In part two, the sensor was taken to full saturation (as in part 1) then exposed to dry $N_2$ from 600–1200 seconds during which time impedance and phase shift data were measure.

The results of the impedance and phase shift measurements are shown in FIGS. 13a and 13b and 14a and 14b, respectively. As shown, the "a" figure and "b" figures when matched up show a symmetric change in impedance and phase shift of the current passing through the polymer, indicating that not only does the impedance of the sensor according to the current invention respond sensitively to the presence of a water analyte, but that the sensor is able to recover and thus can be reused. Specifically, the impedance of the sensor starts at $8.3 \times 10^5$ ohm in FIG. 13a and ends there in FIG. 13b. The low point for the impedance was $\sim 7.6 \times 10^5$ ohms for both parts. This gives an overall change in impedance of $0.7 \times 10^5$ ohms and a percent change of $(0.7/8.3)*100=8.4\%$ in the impedance of the film. The phase shift data shows a high of 39° for FIG. 14a and 38° for FIG. 14b and a low of 33.5° for both 14a and 14b. This corresponds to a difference of 5.5° for 14a and 4.5° for 14b, and a percent change of $(5.5/39)*100=14\%$ and $(4.5/38)*100=12\%$ for 14a and 14b, respectively.

Example 2

Although the use of impedance changes in sensing materials as described herein, have been shown to differentiate between some analytes, the current hybrid sensor is designed to use the additional and simultaneous measurement of change in thickness of the sensing material to increase the resolving power of the sensors, making them more sensitive to type and concentration of analytes.

Figure 15A:
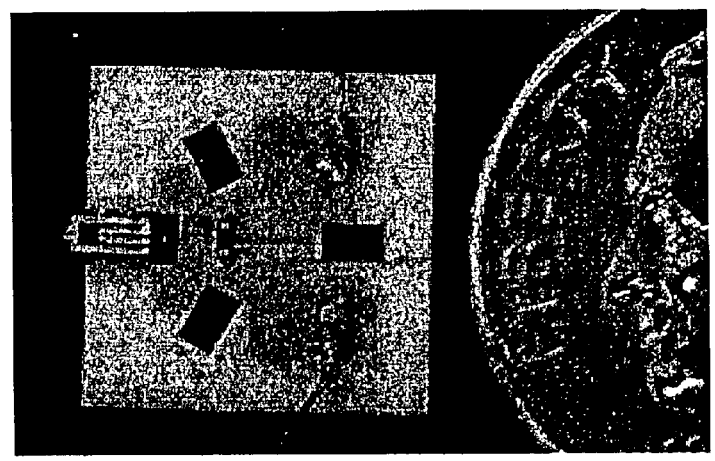
FIG. 15a is a photograph of an exemplary hybrid sensor in accordance with the present invention.

As previously discussed, polymer films swell when exposed to organic vapors. The data shows the thickness response to be characteristic and unique of individual gases and their concentrations. In one embodiment of the current invention, the amount of swelling due to different gases and concentrations is measured using a piezoelectric cantilever placed in contact with one surface of the sensing material. A photograph of one exemplary microcantilever is shown in FIG. 15a.

In such an embodiment the arm of the cantilever is placed in contact with the surface of the sensing material film. Any suitable method of mounting the cantilever arm to the sensing material may be used, such as, for example, by mounting the cantilever to the stage of a scanning force microscope (SFM). The SFM stage gearing and optical microscope allow for minute adjustments in placement of the cantilever tip to the surface of the organic thin film sensing material. This accurately places the tip at the surface and saves the cantilever from damage.

Figure 15B:
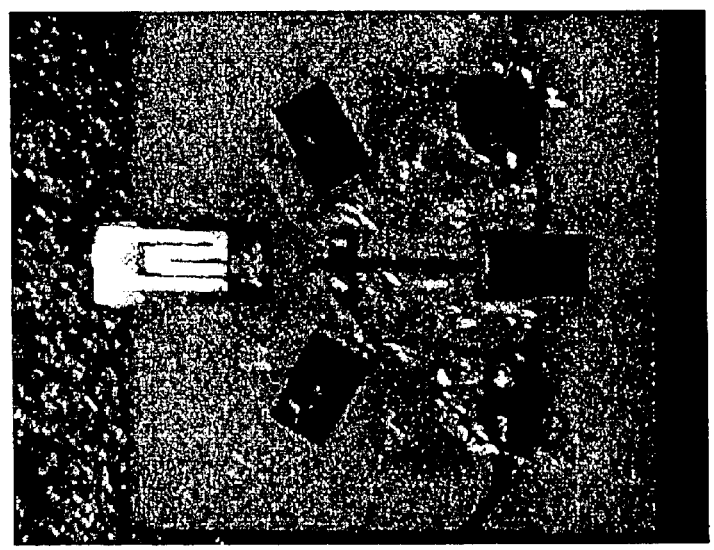
FIG. 15b is a photograph of an exemplary hybrid sensor in accordance with the present invention.
Figure 15C:
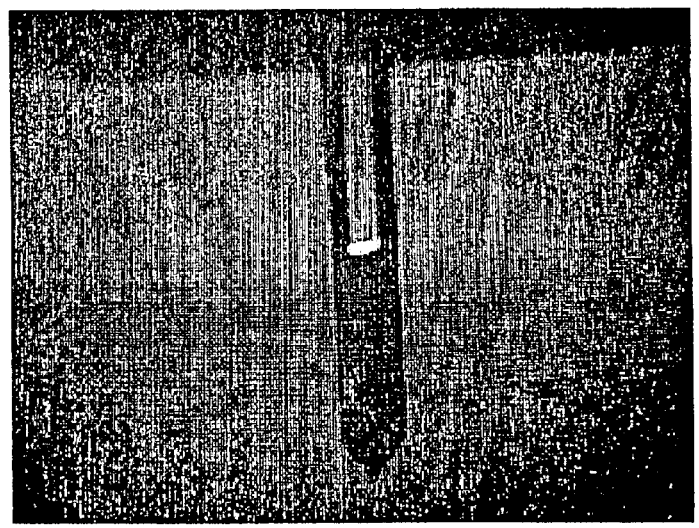
FIG. 15c is a photograph of the microcantilever deflectable arm in an exemplary hybrid sensor in accordance with the present invention.

As shown in FIGS. 15b and 15c, the cantilever is an angled blade attached to a microcircuit. When the blade of the cantilever (shown in close-up in FIG. 15c) makes contact with the surface of the polymer, it bends. The material of the cantilever tip has a permanent dipole moment that changes when the planes of its lattice structure is stressed. Under the stress of bending the internal electric fields change, producing an electric signal. This bending charges the resistance of the circuit attached to the blade from a default value.

As the polymer swells, the blade is bent more, increasing the change in resistance. The resistive response continues to change at a rate of 1–4 milliohms per 1 angstrom of swelling. A conversion constant can be found by averaging the 1–4 milliohm range to 2.5. It follows that 2.5 milliohms equals 1 angstrom and that a 1 ohm response equals 400 angstroms (1Ω=400 Å) of film swelling. This technique was used to determine the effects of different gases on the thickness of a selection of polymers, including PVA, PIB, and poly (ethylene vinyl alcohol) (PEVA). The three different materials were exposed to 5 different vapors. The data collected showed significantly different and unique thickness changes (measured as resistive responses) for each gas exposed to each polymer.

Exemplary sensors as described above were constructed to provide measurements of the thickness changes in sensing materials under standard sensing conditions. In this example a sensor was built and placed in contact with the surface of an iron slug with a thin film sensing material comprising a concentration of 7:1 PEO:Li disposed on top. The sensor and slug were placed on the magnetic mounting stage of an SFM and a cantilever of a sensor was lowered onto the organic thin film surface of each using the optical microscope and gearing of the SFM.

Figure 16:
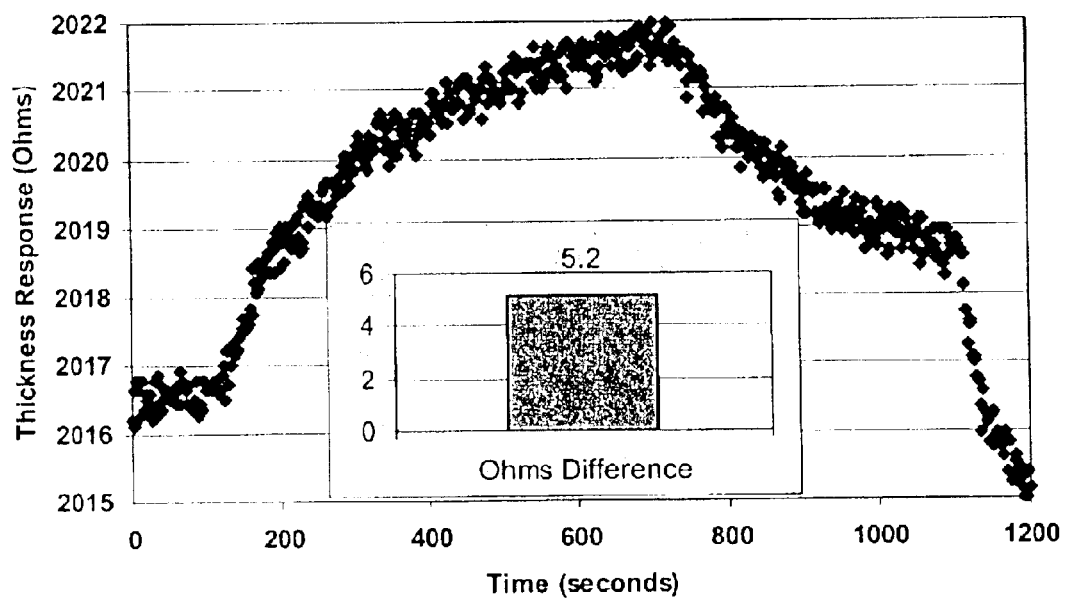
FIG. 16 is a plot of the thickness response of an exemplary hybrid sensor in accordance with the present invention.

The sensors were then exposed to dry $N_2$ gas for 100 seconds, then 100% water vapor was bubbled into the $N_2$ carrier gas from 100–700 seconds, next the sensor was exposed to dry $N_2$ again from 700 to 1100 seconds, and finally the sensor was exposed to atmospheric conditions from 1100 to 1200 seconds. The graph shown in FIG. 16 shows the ohmic change in the cantilever due to the swelling of the organic than film as a function of time. The amount of film swelling can be calculated using the response of the cantilever in the 100 to 700 second range. The difference between the high and low values from 100 to 700 seconds is 5.2 ohms. Using the approximate conversion discussed above of 1 ohm=400 angstroms=0.04 microns an overall thickness change of 2100 angstroms or 0.21 microns can be calculated.

Figure 17A:
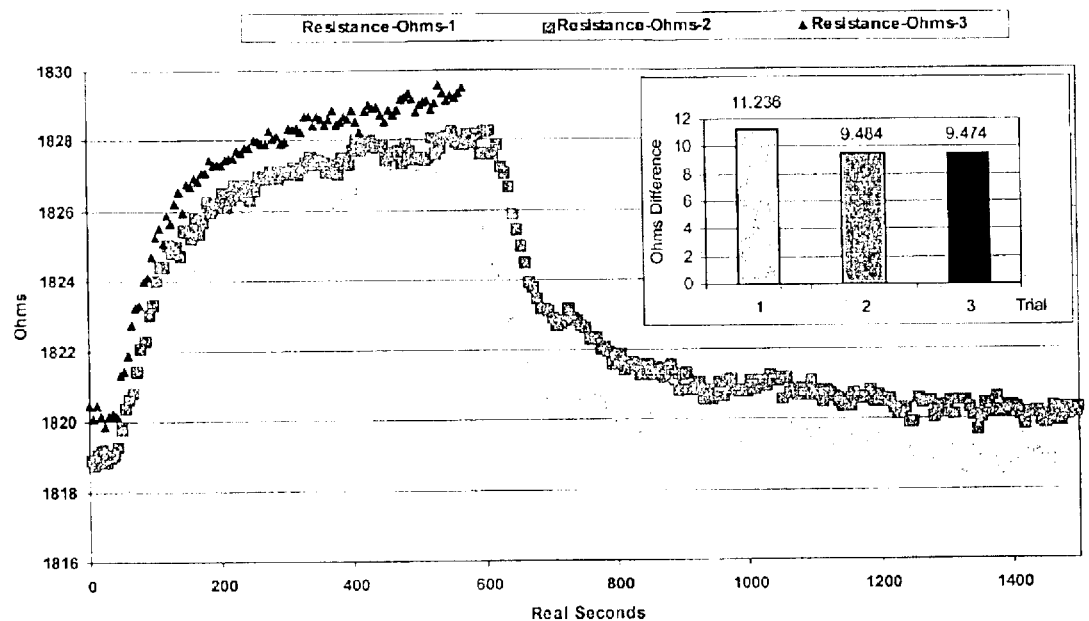
FIG. 17a is a plot of the thickness response of an exemplary hybrid sensor in accordance with the present invention after exposure to a 100% water vapor.
Figure 17B:
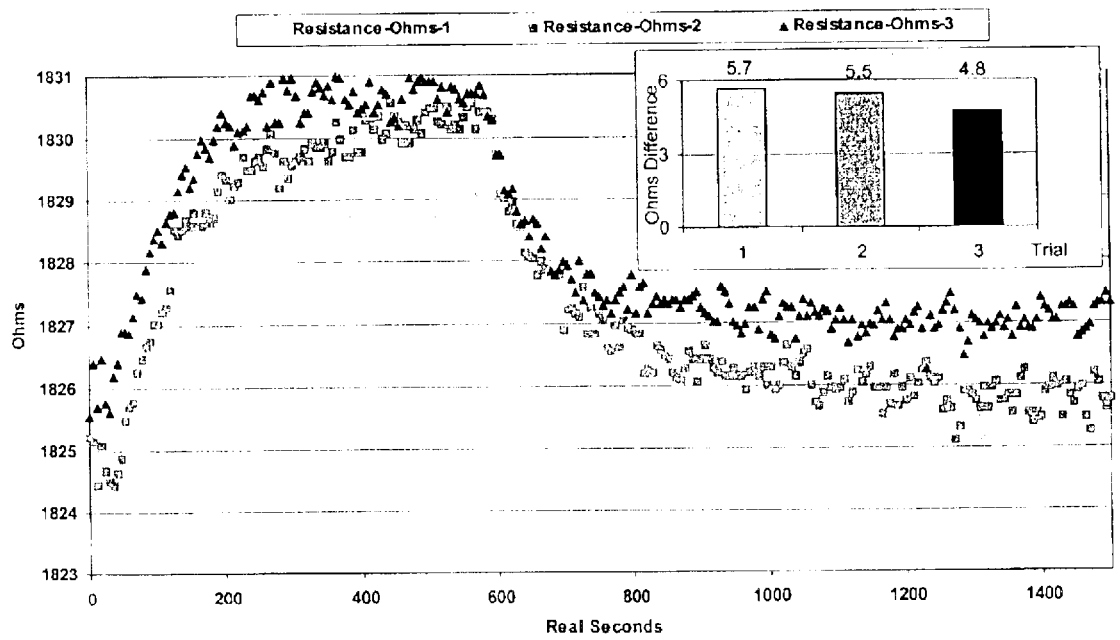
FIG. 17b is a plot of the thickness response of an exemplary hybrid sensor in accordance with the present invention after exposure to a 50% water vapor.

FIG. 17a shows measurements of the thickness response of the sensor in contact with the 7:1 thin film sensing material when subjected to three exposure cycles of 100% water vapor using $N_2$ as the carrier gas, and FIG. 17b shows the sensor when exposed to three cycles of 50% water vapor using $N_2$ as the carrier gas. The slug was mounted and the cantilever placed as before on the SFM stage. The films were exposed to dry $N_2$ for 30 seconds, then water vapor concentration from 30–600 seconds, and dry $N_2$ again from 600–1500 seconds.

The general trends for all of the trials are consistent with one another having a steep initial phase of swelling and a leveling off phase near the saturation point of the material (at 700 s). When exposed to dry $N_2$ the polymer shrank back to nearly its pre swelling level. Each successive trial started at a level slightly above the previous. But the overall difference for each trial remained consistent with only a slight decrease in total difference for each successive run. The thickness response differences for the water vapor exposures were calculated by subtracting the average of the last five high values from the average of the first five low values. This reduced the effect of any extreme data.

The thickness responses for the three 100% water vapor trials were 11.2, 9.5, and 9.5 ohms. For the 50:50 trials the three responses were 5.7, 5.5, 4.8 ohms. These differences are converted into a distance using the 400 angstrom=1 ohms proportion. The median value for the swelling of the thin film in the 100% trial and 50% trial are 3800 angstroms and 2200 angstroms respectively. The original thickness of the entire film was 315,000 angstroms (31.5 microns) measured before the experiment using a Dektak machine in a low humidity environment. Dividing the swelling change by the original thickness and multiplying by 100, percent swelling of 1.2% (100% vapor) and 0.69% (50% vapor) are calculated. Data calculations are summarized in Table 2, below, with median values in bold.

TABLE 2

Thickness Changes at 100% and 50% Water Vapor

| Trial Number and % Water | Ohms Difference | Angstroms Difference | Microns Difference | Film Size Microns | Percent Swelling |
|---|---|---|---|---|---|
| 1–100% | 11.2 | 4500 | 0.45 | 31.5 | 1.4 |
| 2–100% | 9.5 | 3800 | 0.38 | 31.5 | 1.2 |
| 3–100% | 9.5 | 3800 | 0.38 | 31.5 | 1.2 |
| 1–50% | 5.7 | 2300 | 0.23 | 31.5 | 0.7 |
| 2–50% | 5.5 | 2200 | 0.22 | 31.5 | 0.7 |
| 3–50% | 4.8 | 1900 | 0.19 | 31.5 | 0.6 |

As shown, exposure to dry nitrogen, 100% water vapor, and normal atmosphere was shown to produce a significant amount of swelling in the PEO thin film. This effect did not randomly occur, but was consistent to repeated exposure of 100% and 50% water vapor. The effect was also measurable with an increase in thickness of 3800 angstroms when exposed to 100% water vapor. This was a 1.2% increase in overall film thickness. Results at 50% water vapor were half of those at 100% showing film sensitivity to analyte concentration. During consecutive trials of cycled analyte vapor and dry $N_2$ it was observed that the starting point of each cycle was slightly higher than the next and that the differences for each successive run decreased. This was due to residual analyte in the thin film. Longer exposure to dry $N_2$ would allow for the excess analyte to escape from the film and for more consistent starting points.

Example 3

Simultaneous measurements of thickness and impedance changes in the PEO thin film were then conducted using an exemplary piezoelectric cantilever/multimeter and IDA sensor/FRA setup interfaced to a digital processor. Then experiments were conducted to measure thickness and impedance changes simultaneously as the sensor was exposed to analyte vapor and to quantify the relationship between thickness and impedance. Secondarily these experiments were conducted to determine the largest resistance response between 10 Hz and 178 Hz frequencies, and the relationship between the response and solubility parameters.

The first study using the exemplary sensor was performed using 100% water vapor and provides proof that impedance and thickness data can be simultaneously collected and correlate. As shown, the signal produced by the FRA is a sine wave of 178 Hz and 0.1 Volts. During the experiment, the cantilever was lowered and the head cap was placed on the sensor with dry $N_2$ exposure for 15 minutes before measurements were taken. Exposure cycles consisted of dry $N_2$ from 0–30 seconds, then 100% water vapor from 30–570 seconds, and the head cap was taken off for the last 570–600 seconds.

Figure 18A:
FIG. 18a shows an SEM picture of an exemplary PEO sensor material.
Figure 18B:
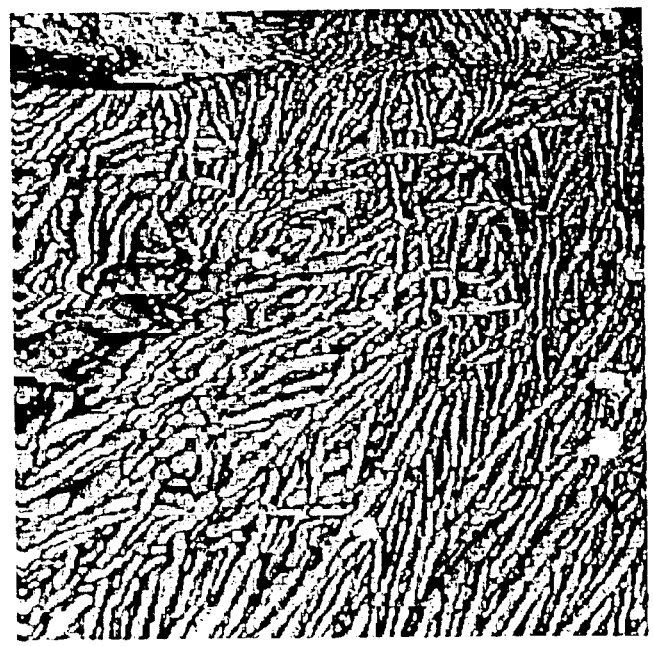
FIG. 18b shows an SEM picture of an exemplary PEO sensor material after exposure to water.

FIGS. 18a and 18b show SFM images of the surface changes that occur when the PEO polymer thin film is exposed to water vapor. The SFM image in FIG. 18a shows a sample of PEO sensing material having a (10:1) PEO:Li ratio, while the sample was exposed to dry $N_2$, and FIG. 18b shows the same sensing material after exposure to a 50:50 (water vapor:dry nitrogen) mix. Topographical and phase contrast scans were taken of the surface at 5 micron levels. The 5 micron phase contrast scans are shown below. As shown, the polymer bundles in FIG. 18b scan are much more pronounced than in the initial scan.

Correlating the imaging experiments with the thickness and impedance measurements it can be shown that metal ion doping levels and analyte exposure of gases change the structure of the polymer strands making them swell and become more electrically conductive.

In addition, imaging of various concentrations of PEO thin films yielded results showing the structure difference between films that were undoped, doped with lithium perchlorate, and heavily doped films. The purpose of the doping is to increase the conductivity of the film. Phase contrast imaging scans were performed on the surface to show the differences between types of material in the film. In the PEO film the dark region dominates the image scan with only thin branching strands of lighter material present. In the doped films the light colored areas bulge and become thicker (21.4:1) with those strands becoming almost disassociated bundles in the highly doped images (7:1). Scans could not be taken on the oily surfaces of the 3:1 and 1:1 scans. Doping levels change the structure within the thin film to shorter and rounder bundles with increased concentration of lithium.

In the scans exposed to water vapor concentrations, shown in FIGS. 18a and 18b, the same effect bulging effect on the long strands was observed. The dry film has apparent strands of light colored material and upon water vapor exposure the strands bulge in the same manner as an increased level of doping showed. In the simultaneous thickness and impedance measurements the impedance drops upon exposure to analyte vapor while the polymer swells and becomes thicker. This leads to the conclusion that doping of a polymer with a conductive salt, or exposure to an analyte gas forms pronounced bundle structures in the polymer film, which increases film thickness and conductivity.

Figure 19:
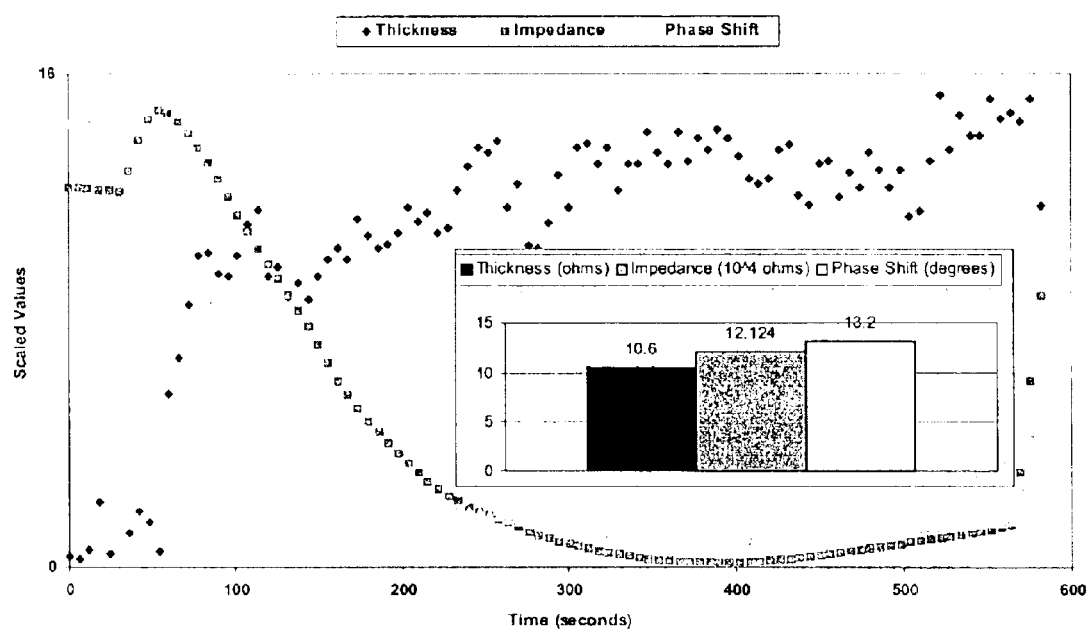
FIG. 19 is a plot of the impedance, thickness and phase shift responses of an exemplary hybrid sensor in accordance with the present invention after exposure to water.

Quantitative results of the study are shown in FIG. 19. The values were scaled to fit all trend lines on the same graph. The overall thickness change was calculated by averaging the last five values of the 30–570 cycle and subtracting them from the average for the first five values from 0–30 seconds. The value calculated was 10.6 ohms converted to a thickness of 4300 angstroms. The impedance change was calculated from the difference of the high value between 0–30 seconds and the low value between 550–570 seconds. The difference was $1.2 \times 10^5$ ohms or 121,200 ohms. The phase angle also drastically changed from a high value of 42.45° to a low value of 29.40° for a difference of 13.05°.

Figure 20:
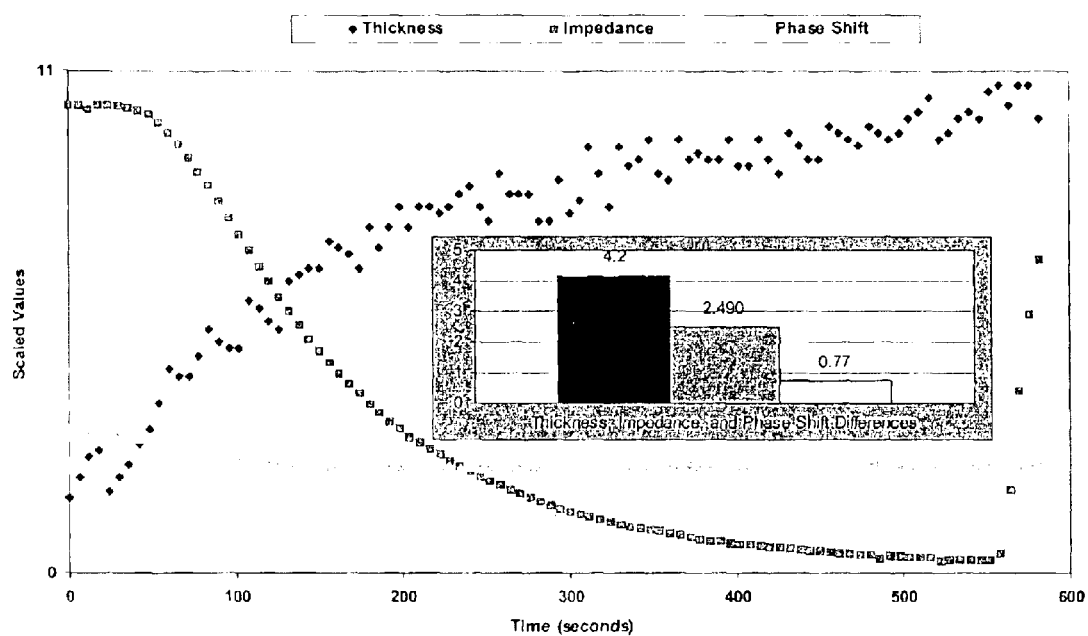
FIG. 20 is a plot of the impedance, thickness and phase shift responses of an exemplary hybrid sensor in accordance with the present invention after exposure to water.
Figure 21:
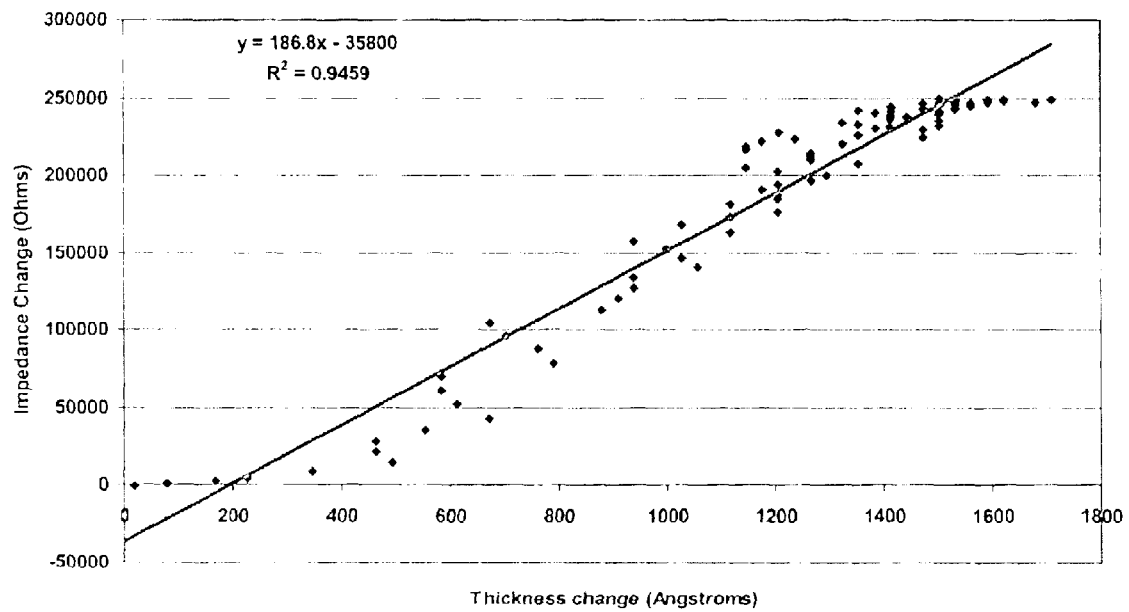
FIG. 21 is a plot correlating the impedance and thickness responses shown in FIG. 20.

Trial 5 of this data set was selected for mathematical modeling to quantify the impedance change per angstrom of thickness change. The graph provided in FIG. 20 shows the thickness, impedance, and phase shift as a function of time with the overall differences of high and low data. The graph in FIG. 21 correlates impedance ($10^5$ ohms) and thickness (ohms) with linear and cubic mathematical best fits. The phase shift is ignored due to its extremely low value of ~3 degrees and change of 0.77 degrees. The graph is symmetric with a linear region in the middle of the data. The last plot models impedance change (ohms) versus thickness (angstroms) with a linear best fit line of:

$$Z = 190 \text{ (ohms/angstroms)} * T - 36{,}000 \text{ (ohms)}$$

The slope correlates every angstrom of swelling to an impedance change (in the negative direction) of 190 ohms. The y-intercept has a value of 36,000 ohms and is related to some type of loading phase of the polymer where the thickness changes with the impedance remaining constant (or actually increasing as was the case in the 178 Hz cases) upon initial gas exposure. The correlation coefficient of $R^2 = 0.9459$ can be improved by limiting the best fit to just the linear region of the graph.

The second study consisted of thickness and impedance measurements of a thin film polymer (7:1 PEO:Li) sensing material exposed to 100% water vapor. Two trials were completed using a signal frequency of 178 Hz and three trials were completed using the frequency of 10 Hz. In each trial the sensor was exposed to 100% water vapor from 0–600 seconds. The sensor was next exposed to dry $N_2$ from 600–1500 seconds. The exception was in trial three were the 100% water vapor was allowed to run until 1200 seconds. Impedance and phase shift data was taken during the first 600 seconds due to the data storage constraint of the FRA.

Figure 22A:
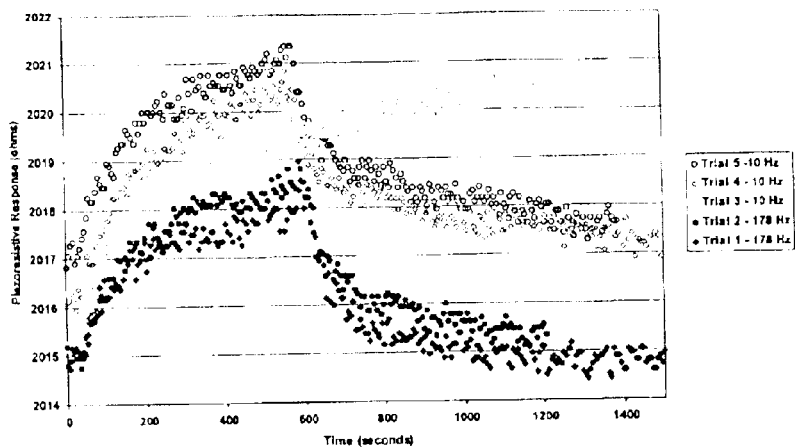
FIG. 22a is a plot of the impedance response at different frequencies of an exemplary hybrid sensor in accordance with the present invention after exposure to water.
Figure 22B:
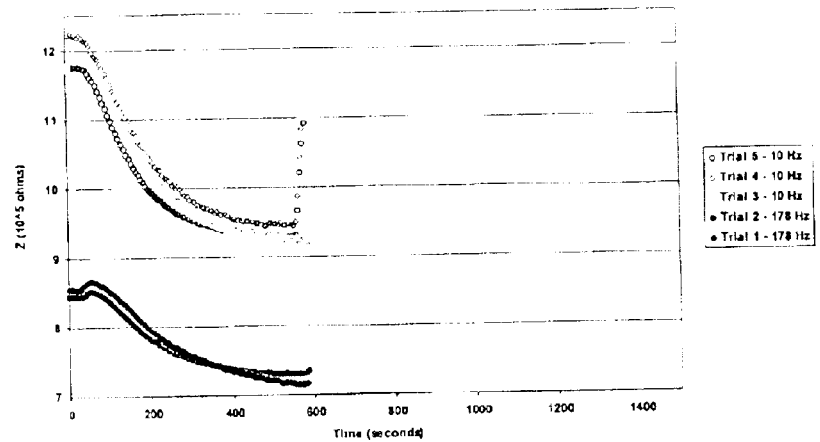
FIG. 22b is a plot of the thickness response at different frequencies of an exemplary hybrid sensor in accordance with the present invention after exposure to water.
Figure 22C:
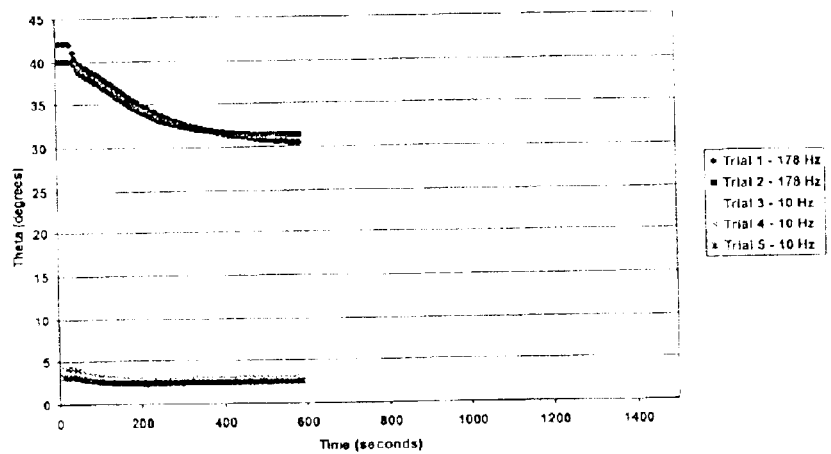
FIG. 22c is a plot of the phase shift response at different frequencies of an exemplary hybrid sensor in accordance with the present invention after exposure to water.
Figure 23A:
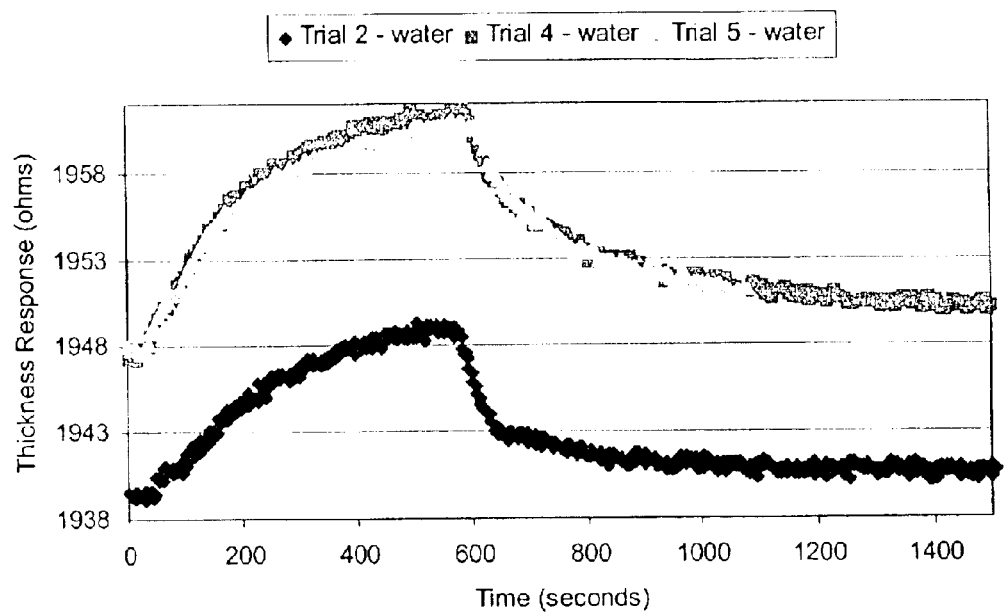
FIGS. 23a and 23b are plots of the impedance and thickness responses of an exemplary hybrid sensor in accordance with the present invention after exposure to water.
Figure 23B:
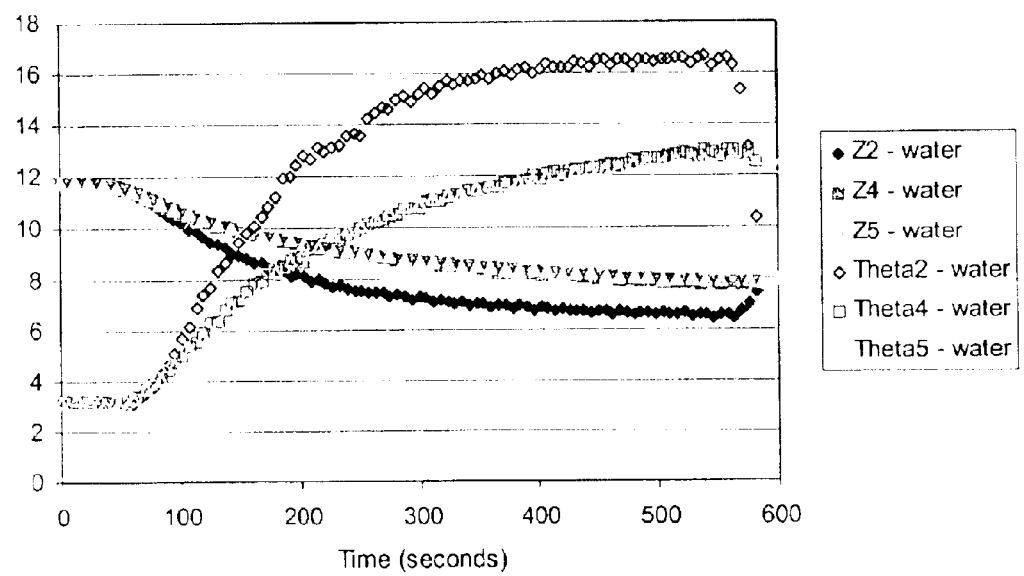
Figure 24A:
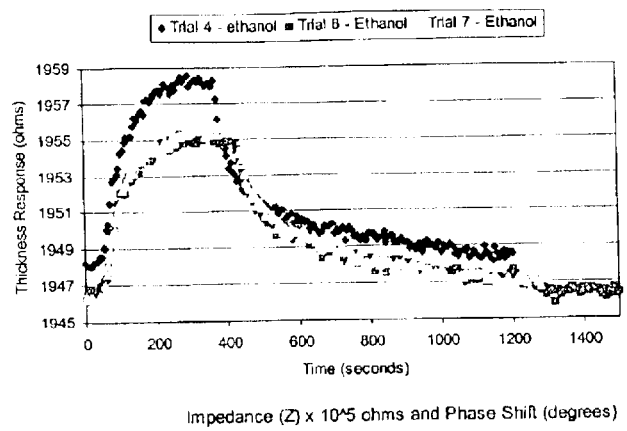
FIGS. 24a and 24b are plots of the impedance and thickness responses of an exemplary hybrid sensor in accordance with the present invention after exposure to 190 proof ethanol.
Figure 24B:
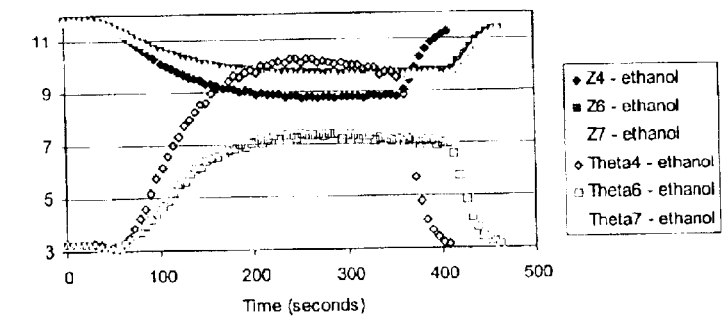
Figure 24C:
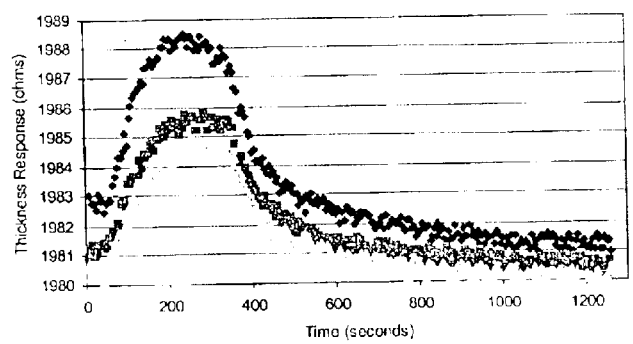
FIGS. 24c and 24d are plots of the impedance and thickness responses of an exemplary hybrid sensor in accordance with the present invention after exposure to 200 proof ethanol.
Figure 24D:
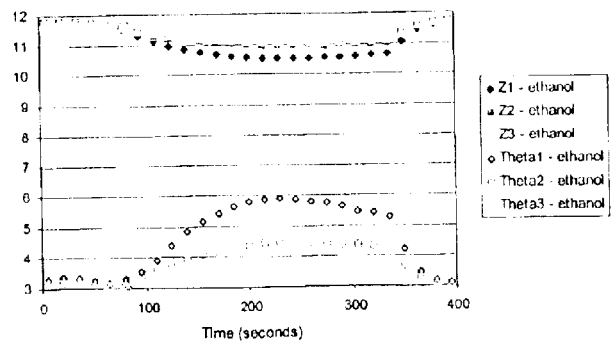
Figure 25A:
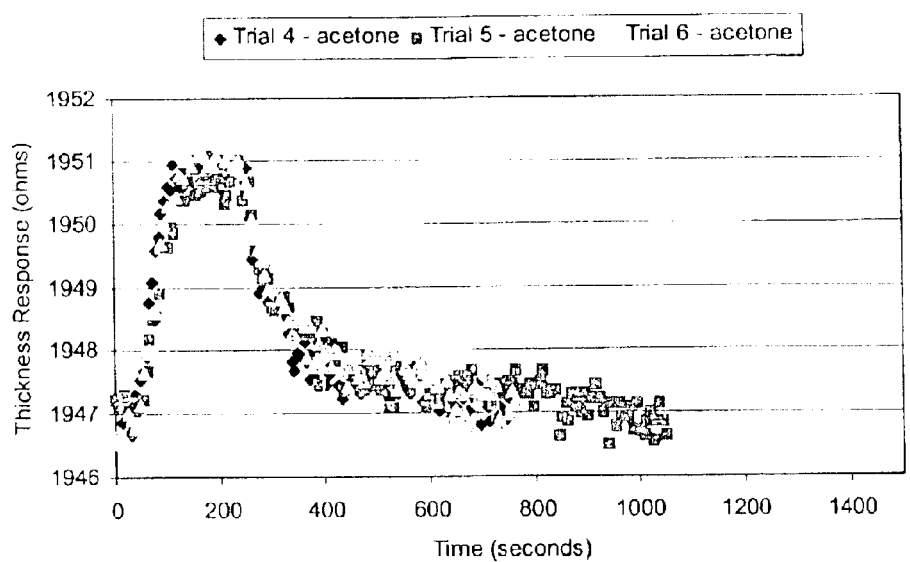
FIGS. 25a and 25b are plots of the impedance and thickness responses of an exemplary hybrid sensor in accordance with the present invention after exposure to acetone.
Figure 25B:
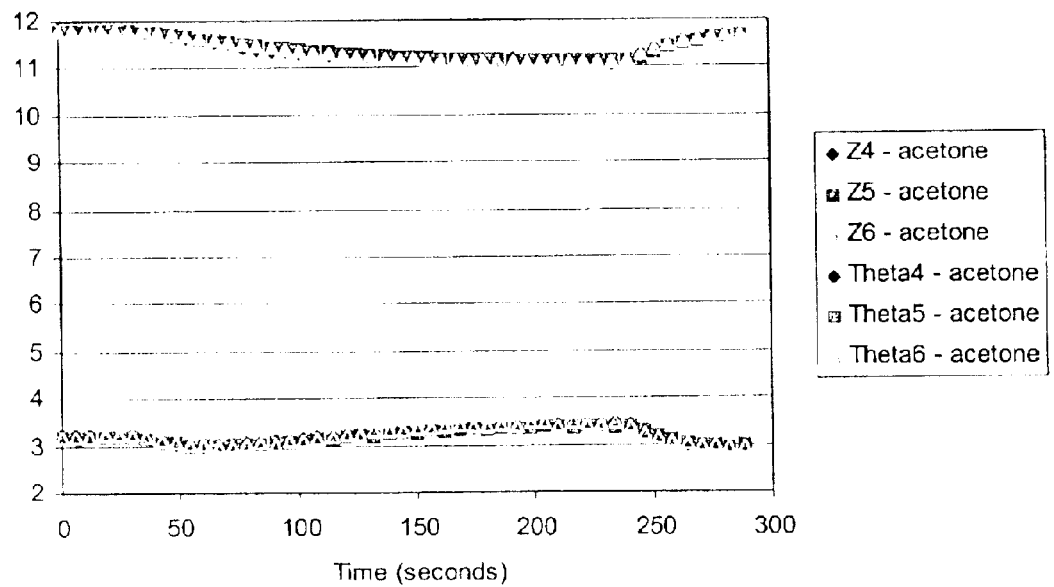
Figure 26A:
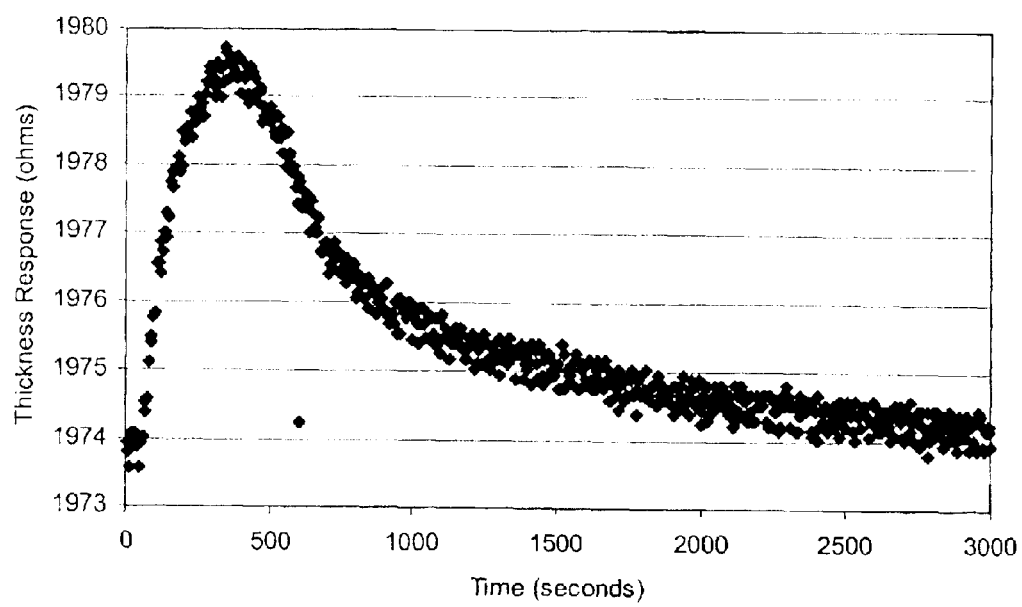
FIGS. 26a and 26b are plots of the impedance and thickness responses of an exemplary hybrid sensor in accordance with the present invention after exposure to n-octane.
Figure 26B:
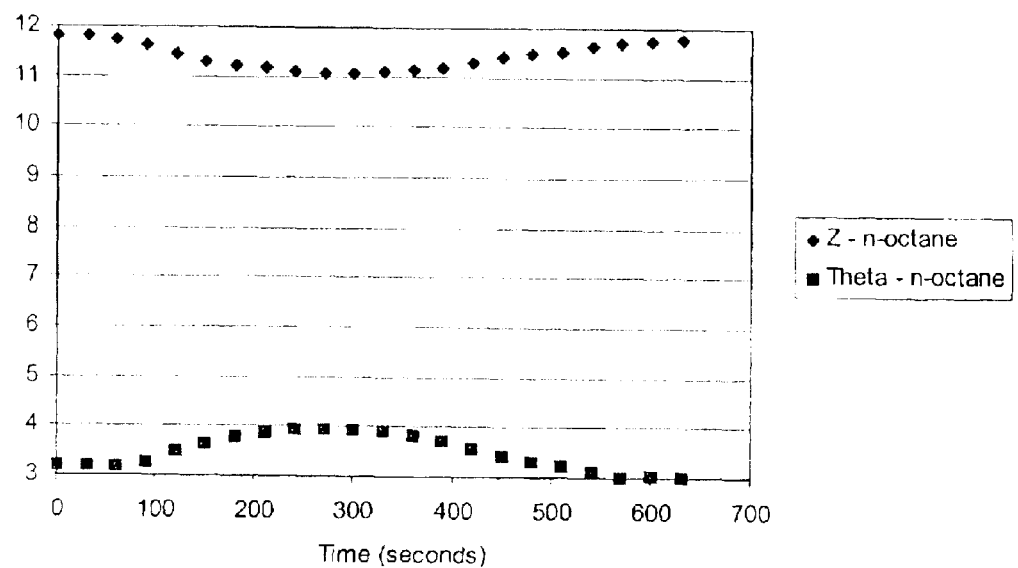

Experiment two data was taken simultaneously but split apart for ease of presentation. Thickness change data is shown in FIG. 22a. The trends are very consistent between the 178 Hz and 10 Hz data. Impedance change data is shown on FIG. 22b. The 10 Hz data starts at a much higher value ~$12 \times 10^5$ ohms with a flat 30–60 second phase. The 178 Hz data starts lower ~$8.5 \times 10^5$ ohms and has an increase in impedance at the initial 30–60 second phase. Phase shift data is shown in FIG. 22c. The 178 Hz data starts high at ~40 degrees and changes significantly. The 10 Hz data starts low ~3 degrees and shows only a minor change of value.

Values for the data taken at 178 Hz show thickness differences between the high and low averages of 2.9 and 3.5 ohms for an average of 3.2 ohms or 1300 angstroms. The impedance changes are calculated from the high and low values of the first and last 30 seconds giving changes of 1.392 and $1.131 \times 10^5$ ohms changes for an average value of $1.262 \times 10^5$ or 126,600 ohms. The phase shift difference was calculated by subtracting the high and low values from the first and last 30 seconds of data. This returned values of 11.71 and 8.80 degrees for an average of 10.26 degrees.

Values for the data taken at 10 Hz were calculated similarly to the 178 Hz calculations and give thickness changes of 4.0, 4.3, 4.2 ohms for a median value of 4.2 ohms or 1700 angstroms. The impedance data shows differences of 2.535, 2.812, and $2.490 \times 10^5$ ohms for a median value of $2.535 \times 10^5$ ohms or 253,500 ohms. The phase shift differences were 1.48 and 0.77 degrees for an average of 1.13 degrees.

As shown, there are large differences between the impedances measured by the 178 Hz and 10 Hz cases with the 10 Hz signal returning a more robust response. The differences in thickness values, however, are only slightly different and require further analysis. The phase shift data shows an expected high change in angle for the 178 Hz and virtually no change of angle for the 10 Hz. Table 3, below summarizes the difference data for the frequency changes.

TABLE 3

Summary of Changes at 178 Hz and 10 Hz

| Accepted values | Thickness Difference | Impedance Difference | Phase Shift Difference |
| --- | --- | --- | --- |
| 178 Hz | 1300 angstroms | 126,600 ohms | 10.26 degrees |
| 10 Hz | 1700 angstroms | 253,500 ohms | 1.13 degrees |

The third study consisted of measurement of thickness and impedance changes in a sensor having a sensing material (10:1 PEO:Li) upon exposure to the analyte vapors water, ethanol, acetone, and n-octane. The trials were performed for each vapor at a 100:0 analyte:dry $N_2$ ratio. For the water trials, dry $N_2$ was exposed to the sensor from 0–30 seconds, a 100:0 mixture from 30–530 seconds, and dry $N_2$ again for the final 530–4200 seconds. For the ethanol trials, dry $N_2$ was exposed to the sensor from 0–30 seconds, a 100% mixture of ethanol vapor from 30–360 seconds, and dry $N_2$ for the last 360–2500 seconds. Finally, for the acetone trials the exposure cycle was dry $N_2$ from 0–30 seconds, 100% acetone vapor from 30–240 seconds, and dry $N_2$ from 240–900 seconds. The cycles varied in time, dependent upon how quickly the analyte vapor was absorbed into the PEO film and also how quickly it exited the material.

Figure 27:
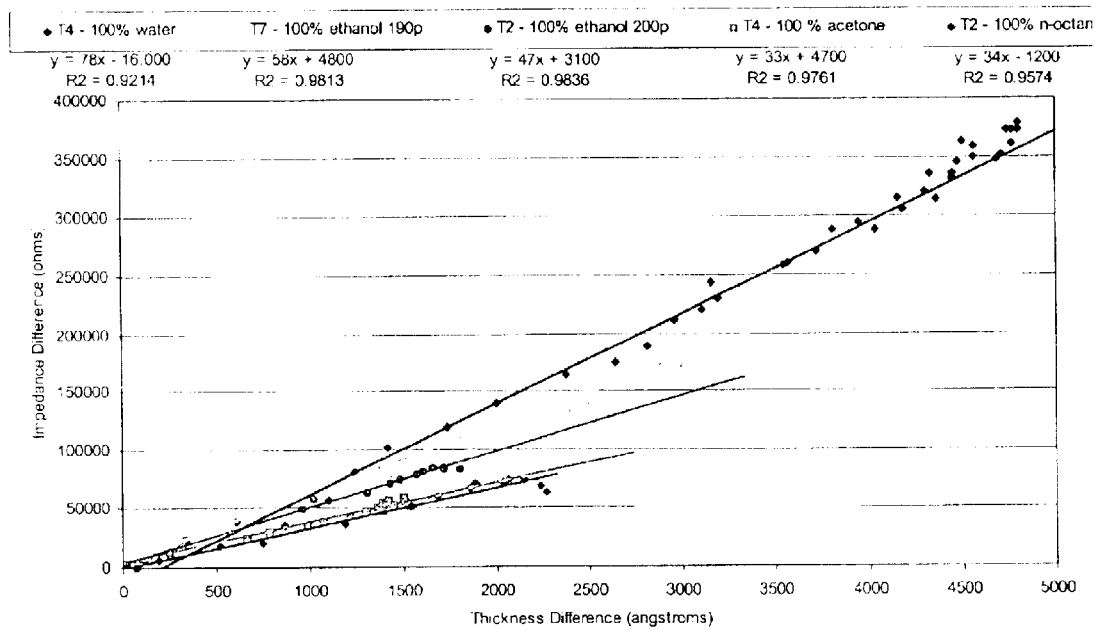
FIG. 27 is a plot of thickness versus impedance responses for the data shown in FIGS. 23 to 26.

Experiment three results for 100% water, ethanol (190 and 200 proof), acetone, and n-octane vapor exposures appear in the FIGS. 23 to 26 and summarized in Table 4 and FIG. 27. Three trials were completed for each analyte at 100% concentration. For each trial of each analyte, dry nitrogen gas was blown into the head cap from 0–30 seconds to determine baseline thickness and impedance readings. The sensor was then exposed to 100% analyte vapor until the thickness and impedance readings leveled off, at this point it was deemed that the polymer was fully saturated. The last phase was again dry nitrogen gas passed over the sensor until readings went back to the baseline. Three trials were completed at 100% vapor for water, ethanol (190p and 200p), acetone and n-octane. The median trial of each analyte was graphically and mathematically modeled during its swelling phase for the relationship between impedance changes per angstrom change of thin film swelling.

TABLE 4

Summary of Differences for Water, Ethanol, and Acetone

| Analyte Vapor | Thickness Difference (increase) ($\Omega$) | Thickness Change (Å) | Impedance Difference (decrease) ($\Omega$) | Phase Shift Difference (increase) ($\theta$) |
|---|---|---|---|---|
| Water | 9.5 | 3800 | 527,100 | 13.43 |
| Water | 13.6 | 5400 | 399,000 | 9.76 |
| Water | 12.8 | 5100 | 390,800 | 9.46 |
| Solubility Parameter | = 48 Mpa$^{1/2}$ | Saturation Vapor Pressure | = 21 torr | |
| Ethanol (190p) | 10.1 | 4000 | 293,700 | 6.28 |
| Ethanol (190p) | 8.6 | 3400 | 210,100 | 4.00 |
| Ethanol (190p) | 9.4 | 3800 | 219,600 | 4.34 |
| Solubility Parameter | = 26–48 Mpa$^{1/2}$ | Saturation Vapor Pressure | = 21–52 torr | |
| Acetone | 3.8 | 1500 | 64,300 | 0.21 |
| Acetone | 3.5 | 1400 | 62,300 | 0.21 |
| Acetone | 4.4 | 1800 | 67,100 | 0.20 |
| Solubility Parameter | = 20.5 Mpa$^{1/2}$ | Saturation Vapor Pressure | = 212 torr | |
| Ethanol (200p) | 5.2 | 2100 | 115,800 | 2.06 |
| Ethanol (200p) | 4.3 | 1700 | 79,100 | 1.14 |
| Ethanol (200p) | 4.0 | 1600 | 67,300 | 0.88 |
| Solubility Parameter | = 26 Mpa$^{1/2}$ | Saturation Vapor Pressure | = 52 torr | |
| n-octane | 16.8 | 6700 | ~100,000 | small |
| n-octane | 5.2 | 2100 | 73,900 | 0.78 |
| n-octane | 0.4 | 200 | −800 (increase) | −0.05 |
| Solubility Parameter | = 14.1 Mpa$^{1/2}$ | Saturation Vapor Pressure | = 45 torr | |

In the analytes tested all of the trials showed a thickness increase (swelling), an impedance drop (increased conductivity), and a phase shift increase (except trial 3 of n-octane). The thickness, impedance, and phase shift differences were calculated using the average of the last five data points collected under analyte exposure subtracted from the average of the first five pre-exposure baseline points (the difference taken to yield a positive value). The median value between each of the three trials per analyte was determined to be the accepted value. This data along with the solubility parameters and saturation vapor pressures of each analyte have been listed in Table 4, above. Three items will be addressed for each organic analyte including the response ($\Delta T$, $\Delta Z$, and $\Delta$time to saturation), the recovery time (time to return to baseline state), and any issues that arose during tests.

Of the analytes tested water (FIG. 23) had the largest thickness (12.8$\Omega$, 5100 Å) and impedance (399,000$\Omega$) responses but took the longest time to reach saturation (30–540 seconds). It also had the longest recovery time at ~4200 second or 70 minutes. Water also is the farthest from PEO in solubility parameter (48 Mpa$^{1/2}$) and has the lowest saturation vapor pressure (21 torr).

Ethanol 190 proof (FIG. 24) had the next largest thickness (9.4$\Omega$, 3800 Å) and impedance (219,000$\Omega$) responses with a large time to saturation (30–420 seconds). The recovery time was long at ~1500 seconds. Ethanol 190 proof has a large amount of water in it resulting in larger values than pure ethanol would return. The solubility parameter and saturation vapor pressures are given as ranges (in Table 4) from pure ethanol to water due to the unknown concentration of water in the sample. Ethanol 200 proof has less water in it than 190 proof and showed smaller thickness (4.3$\Omega$, 1700 Å) and impedance (79,100$\Omega$) responses than its counterpart (190 proof). The time to saturation was shorter as well at 30–330 seconds. The recovery time was comparable to acetone at ~1000 seconds. Due to the smaller water content 200 proof thickness and impedance changes are smaller and the time to saturation was faster than 190 proof.

Acetone (FIG. 25) had the smallest thickness (3.8$\Omega$, 1500 Å) and impedance (64,300$\Omega$) changes with the fastest time to saturation (30–240 seconds). The recovery time was also the shortest at ~1000 seconds. Acetone also has the highest saturation vapor pressure of 212 torr.

For n-octane, (FIG. 26) the thickness was measured from 16.8$\Omega$ to 0.4$\Omega$ (6700 Å to 200 Å) with a median of 5.2$\Omega$ (2100 Å). The impedance changes were from ~100,000$\Omega$ decrease to an 800$\Omega$ increase with a median value of 73,900$\Omega$ decrease. All of the responses were slow to reach saturation (30–530 seconds). The recovery time ranged from never recovering to ~3000 seconds (50 minutes). The trials decreased from trial 1 to 3 with a large range in values.

Finally, the modeling of the swelling phase of the sensing material for each analyte is shown in FIG. 27. The equations are given at the top with water having the largest impedance per angstrom change of 78$\Omega$/Å. N-octane and acetone are the lowest at 34$\Omega$/Å and 33$\Omega$/Å respectively. The equations transform using y=$\Delta Z$ and x=$\Delta T$ all with correlation coefficients from 0.90–1.00:

Water: $\Delta Z=78(\Omega/\text{Å})\Delta T+16,000\Omega$

Ethanol 190p: $\Delta Z=58(\Omega/\text{Å})\Delta T+4800$

Ethanol 200p: $\Delta Z=47(\Omega/\text{Å})\Delta T+3100$

Acetone: $\Delta Z=33(\Omega/\text{Å})\Delta T+4700$

N-octane: $\Delta Z=34(\Omega/\text{Å})\Delta T-1200$

In the figure, the slope is the rate of change of the impedance (in ohms) per angstrom of swelling in the polymer thin film sensing material. The y-intercept may refer to some kind of loading phase due to pre-swelling changes in the polymer. These equations show the behavior of the thin film sensing material during the swelling phase of the polymer after analyte exposure until saturation of the sensing material occurs. As indicated the sensing material responds differently to each analyte providing a composite thickness/impedance "fingerprint" allowing for the capability of identifying unknown analytes in a sample.

Specifically, the modeling equations show a signature slope for each analyte. The slope refers to the change in impedance per angstrom of swelling. Water had the largest slope at 78$\Omega$/Å and acetone and n-octane tied for the lowest at 33$\Omega$/Å and 34$\Omega$/Å respectively. Using time to saturation as an additional parameter, the acetone and n-octane are readily differentiable because of acetones short time to saturation (190 seconds) compared to n-octanes long time to saturation (500 seconds). These relationships could be useful in the prediction and identification of gases. The modeling equations give relationships of the thin film PEO responses to specific gases and concentrations The time to saturation upon analyte exposure decreased as the solubility parameter got closer to PEO's value of 24.2

Figure 28A:
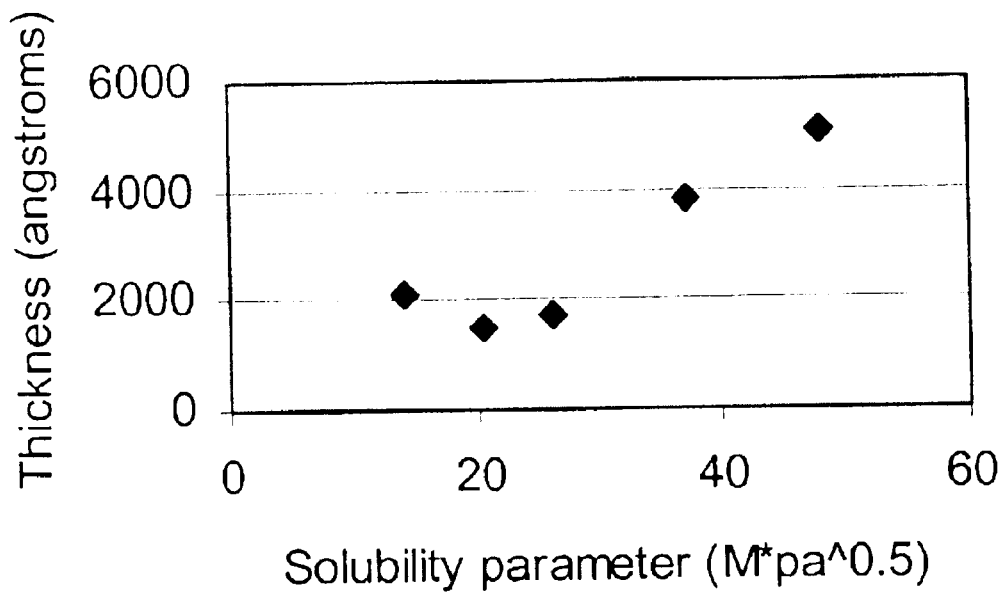
FIGS. 28a and 28b are plots of thickness and impedance responses versus solubility parameter, respectively, for the data shown in FIGS. 23 to 26.
Figure 28B:
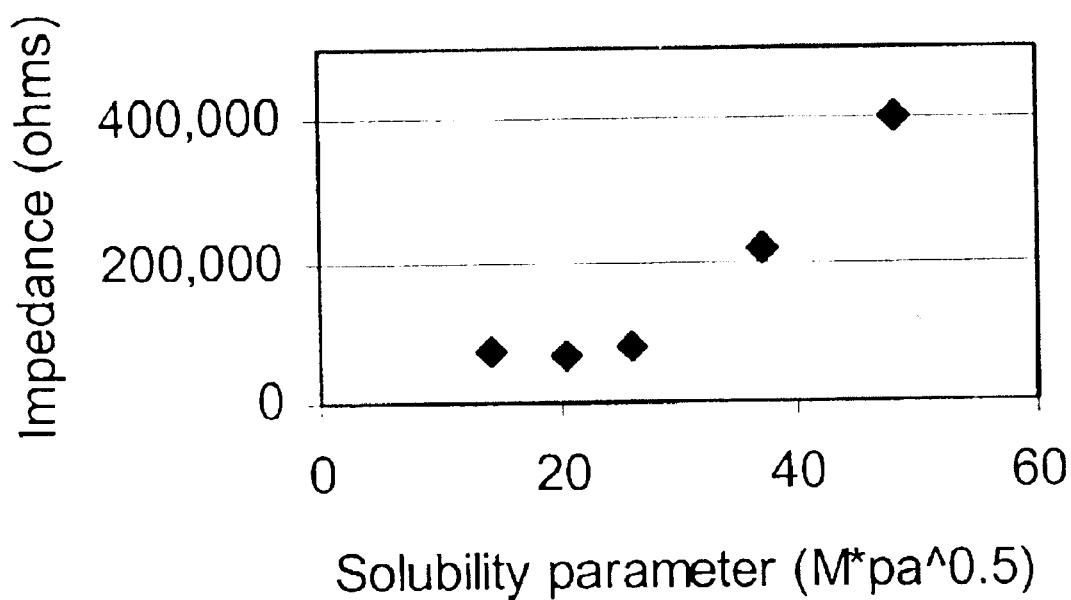

Mpa$^{1/2}$ and as saturation vapor pressure increased. Acetone (20.5 Mpa$^{1/2}$, and 212 torr) and ethanol 200p (26 Mpa$^{1/2}$, and 52 torr) had the fastest times to saturation and water (48 Mpa$^{1/2}$ with the solubility parameter the farthest from PEO; 21 torr the lowest saturation vapor pressure) was the slowest to saturate the polymer. The thickness changes and impedance changes are correlated on plots verses solubility parameter in FIGS. 28a and 28b, showing the same general response curves. The value of PEO found in the exemplary tests run in accordance with the current invention may be different than the standard value of 24.2 because the PEO in these experiments was doped with Li+.

Example 4

Although the above results prove that the hybrid sensors in accordance with the present invention are able to accurately and uniquely identify different analytes, the sensors of the current invention are also able to quantify the concentration of a particular analyte in a sample. Accordingly, a study was conducted to quantify the sensitivity of the hybrid sensor to vapor concentration. Thickness and impedance changes were measured in an exemplary sensor upon exposure to concentrations of 100%, 75%, 50%, and 25% of analyte vapor in nitrogen carrier gas. Analyte concentrations were tested using the four analytes water, ethanol, acetone, and n-octane. After baseline thickness and impedance levels were achieved using dry nitrogen, varying concentrations were delivered until the sensor thin film was saturated. Dry nitrogen was reapplied until the baseline reading in thickness was matched.

Figure 29A:
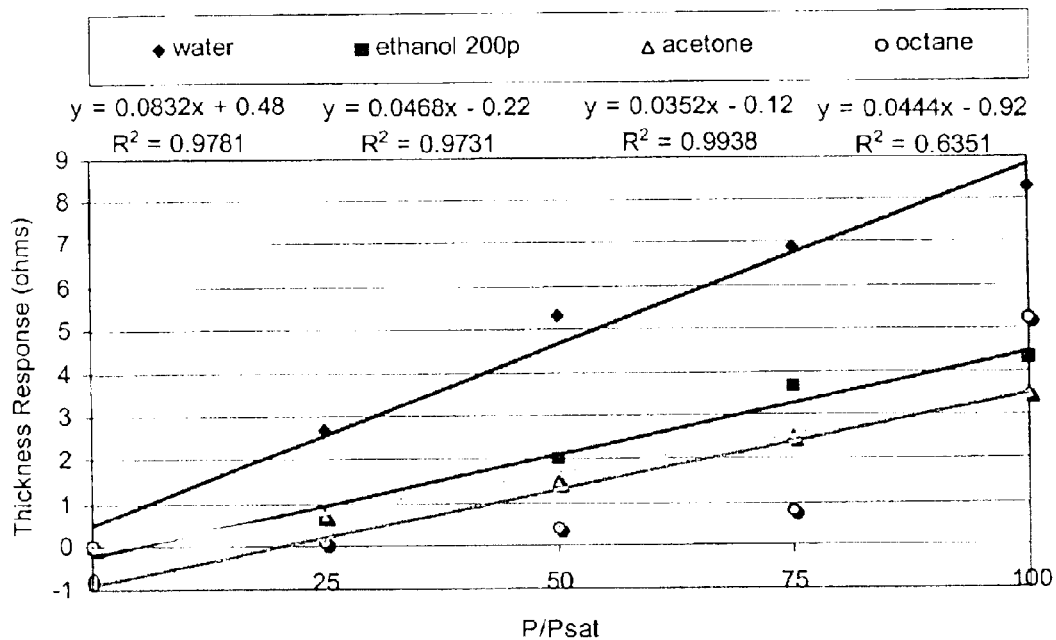
FIG. 29a is a plot of thickness versus concentration responses for an exemplary hybrid sensor in accordance with the current invention when exposed to water, ethanol (200 proof), acetone, and n-octane.

Trials were done in succession and are summarized in Table 5. The percent change for $\Delta T$ and $\Delta Z$ from levels established at 100% vapor were calculated for each concentration. Graphical and mathematical models were developed for the thickness change verses $P/P_{sat}$ (percent concentration of analyte compared to concentration at 100% saturation) in FIG. 29a. Additional modeling was performed on acetone to determine the rate of impedance change per angstrom of swelling for each concentration 100%–25% in FIG. 29b.

A definite trend is shown in the varying concentration data. For all four analytes the difference in peak height for the thickness response decreases as the percent concentration of vapor decreases. This relationship between thickness change and percent concentration is shown in the linear best fits with correlation coefficients near 1.00 in FIG. 29a and indicates that the sensors of the current invention are able to provide quantitative information about the concentration of a particular analyte in a sample. N-octane is the only exception, its linear fit has a poor correlation coefficient of 0.6351 and would best be fit by an exponential curve. As shown, in water (as in ethanol and acetone) as the percent concentration in analyte vapor decreases (100%, 75%, 50%, to 25%) so does the percent thickness change (100%, 83%, 64%, to 33%). The impedance does not follow this linear trend (100%, 60%, 17%, to 3%). Once again n-octane is the exception as neither change in thickness or impedance follow the linear decrease in 25% steps. The results of this study are summarized in Table 5.

Figure 29B:
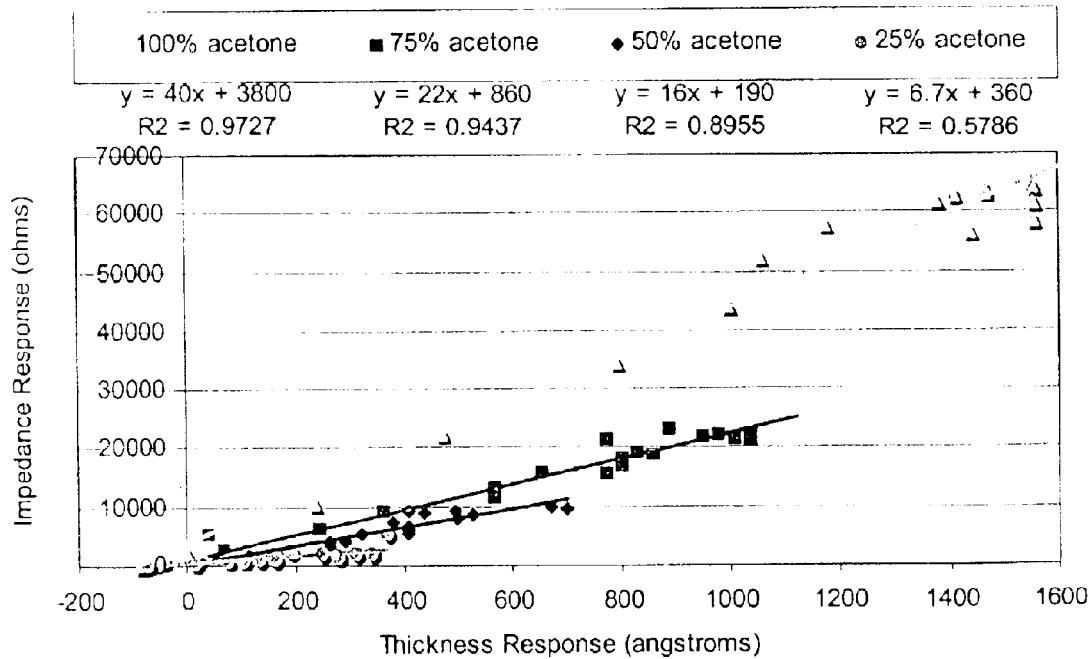
FIG. 29b is a plot of thickness versus impedance responses for an exemplary hybrid sensor in accordance with the current invention when exposed to varying concentrations of acetone.

FIG. 29b models the response of the thin film sensor material to acetone at varying concentration. Each concentration has a different linear best fit, the slope is different for each trial. This shows that the impedance change per angstrom not only changes with analyte vapor, but with concentration of that vapor. The slopes are 40Ω/Å at 100%, 22Ω/Å at 75%, 16Ω/Å at 50%, and 6.7Ω/Å at 25%. The percent of full saturation is 100%, 55%, 40%, and 17% respectively. This does not fit a linearly decreasing trend. However, if we use the equation of the median trial for acetone ($\Delta Z=33\Delta T+4700$ from the 100% concentration experiments earlier) the slope value was 33Ω/Å and the percent calculations change to fit the linearly decreasing trend: 100%, 67%, 49%, and 20%. Modeling equations are summarized in Table 6, below, where y=$\Delta Z$ and x=$\Delta T$.

TABLE 5

Responses to Changes in Vapor Concentrations (P/Psat)

| Analyte | 100% | 75% | 50% | 25% | 100% |
|---|---|---|---|---|---|
| Water: $\Delta T$ | No trial | 6.9 | 5.3 | 2.7 | 8.3 |
| Water: $\Delta Z$ | | 173,600 | 49,800 | 8,200 | 289,500 |
| Water: Ω | | 3.52 | 0.55 | −0.09 | 7.55 |
| ($\Delta T/\Delta T_{sat}$)100 | (6.9/8.3)100 | =83% | 64% | 33% | 100% |
| ($\Delta Z/\Delta Z_{sat}$)100 | (1.736/2.895)100 | =60% | 17% | 3% | 100% |
| Ethanol 200p: $\Delta T$ | 4.3 | 3.7 | 2.0 | 0.6 | No trial |
| Ethanol 200p: $\Delta Z$ | 79,100 | 48,000 | 15,600 | 3,700 | |
| Ethanol 200p: Ω | 1.14 | 0.45 | −0.05 | −0.14 | |
| ($\Delta T/\Delta T_{sat}$)100 | 100% | 86% | 47% | 14% | |
| ($\Delta Z/\Delta Z_{sat}$)100 | 100% | 61% | 20% | 5% | |
| Acetone: $\Delta T$ | 3.5 | 2.5 | 1.5 | 0.7 | No trial |
| Acetone: $\Delta Z$ | 45,800 | 22,100 | 9,600 | 2,000 | |
| Acetone: Ω | 0.08 | −0.15 | −0.20 | −0.13 | |
| ($\Delta T/\Delta T_{sat}$)100 | 100% | 71% | 43% | 20% | |
| ($\Delta Z/\Delta Z_{sat}$)100 | 100% | 48% | 21% | 4% | |
| n-octane: $\Delta T$ | 5.2 | 0.8 | 0.4 | 0.1 | 0.4 |
| n-octane: $\Delta Z$ | 73,900 | 700 | −300 | −400 | −800 |
| n-octane: Ω | 0.78 | −0.08 | −0.04 | −0.02 | −0.05 |
| ($\Delta T/\Delta T_{sat}$)100 | 100% | 15% | 8% | 2% | 8% |
| ($\Delta Z/\Delta Z_{sat}$)100 | 100% | 11% | −0.4% | −0.5% | −11% |

TABLE 6

Relationship Between Slopes and Concentration of Vapor Present

| Concentration | 100% | 75% | 50% | 25% |
|---|---|---|---|---|
| Equation | y = 40x + 3800 | y = 22x + 860 | y = 16x + 190 | y = 6.7x + 360 |
| Percent of $P_{sat}$ | 40/40*100 = 100% | 22/40*100 = 55% | 40% | 17% |
| Median from figure 45 | y = 33x + 4700 33/33*100 = | 22/33*100 = | 16/33*100 = | 6.7/33*100 = |
| Percent of $P_{sat}$ | 100%~100% | 67%~75% | 49%~50% | 20%~25% |

Figure 30:
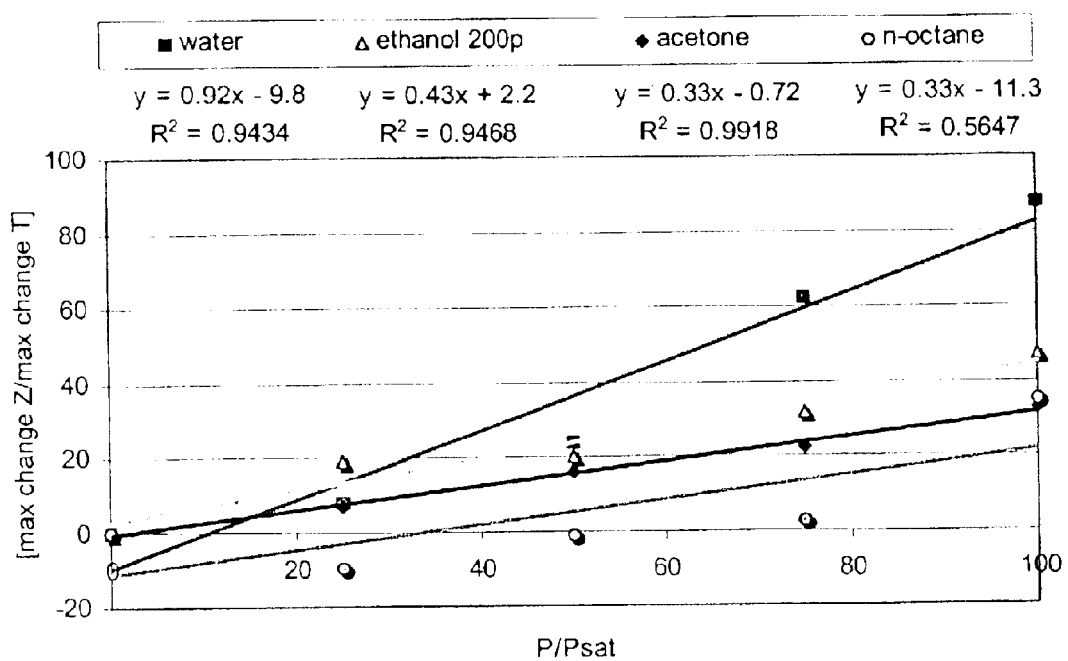
FIG. 30 is a plot for identifying and quantifying an analyte in a sample based on measurement obtained using an exemplary hybrid sensor in accordance with the present invention.

The final modeling of FIG. 30 shows best fit lines for the four analytes. The slope is in units of $[(\Omega/\text{Å})/(\%$ concentration)] and identifies the analyte vapor present. Distance along the line shows the concentration of vapor present from 0% to 100%.

As shown, the sensor shows sensitivity to percent concentration of analyte vapor. Thickness verses time plots show a definite decreasing change in thickness response as percent analyte is reduced. With decreased vapor concentration results decreased thickness change. The $\Delta T$ verses P/Psat shows an increasing linear relationship between change in thickness and increasing concentration of analyte vapor for 3 of the 4 analytes tested. As analyte concentration is increased, the thickness response increases as well.

N-octane was the exception having a poor linear best fit shown by the low correlation coefficient of 0.6351. The trials performed from 100% to 25% concentration show a better fit exponentially in the change in thickness. This deviation from linearity may be due to the interaction of n-octane $(CH_3(CH_2)_6CH_3)$ with the molecularly similar PEO ($—CH_2CH_2O—$). Some type of bonding or filling of the conductive regions in the polymer matrix, may account for the lack of recovery after film swelling, the diminished response, and the small impedance change.

Modeling performed on acetone shows that the decrease in impedance per angstrom of swelling is dependent not only on type of analyte (as shown previously) but dependent upon concentration present. For example, the modeling equation for 100% acetone vapor has a slope of 33$\Omega$/Å and was used as a saturation reference. At 75% concentration the slope (22$\Omega$/Å) was 67% of the reference, at 50% vapor the slope (16$\Omega$/Å) was 49% of the reference, and at 25% vapor the slope (6.7$\Omega$/Å) was 20% of the reference (a direct relationship). As percent concentration of vapor decreases, $\Delta Z/\Delta T$ changes by an equivalent amount.

Mathematical modeling provides a set of best fit plots that can be used to identify the type and concentration of vapor. The slope identifies which of the four different vapors are present. The distance along the line identifies the concentration of vapor present. Accordingly, Applicants have shown that by taking readings of thickness and impedance change at two different unknown concentrations, the type and concentration of analyte gas can be determined by a hybrid sensor in accordance with the present invention.

Using these exemplary relationships, the hybrid sensors of the current invention can be used to not only identify, but quantify unknown analytes in a sample. It should be understood that while exemplary sensors, analytes, and relationship are described in the examples above, these are only provided as evidence of the efficacy of the current sensors, and that the same types of relationships can be determined and calculated for any sensor combination capable of measuring impedance and thickness changes in a sensing material simultaneously in response to the presence of a particular analyte.

Figure 31A:
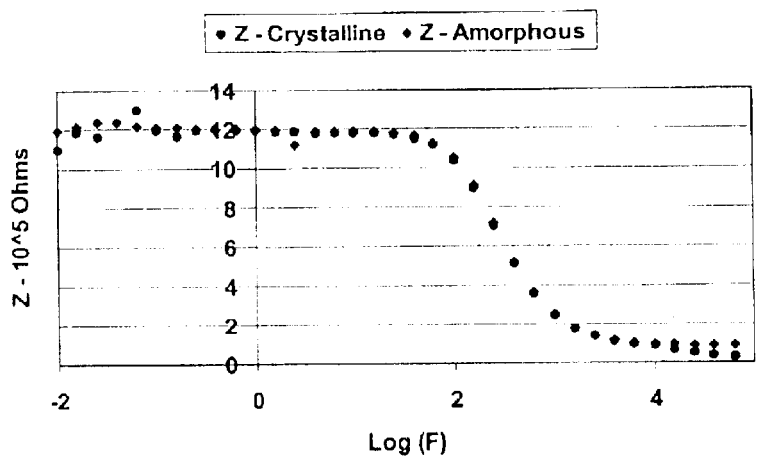
FIGS. 31a, 31b, and 31c show plots of measurements taken with an exemplary amorphous polymer material in accordance with the present invention.
Figure 31B:
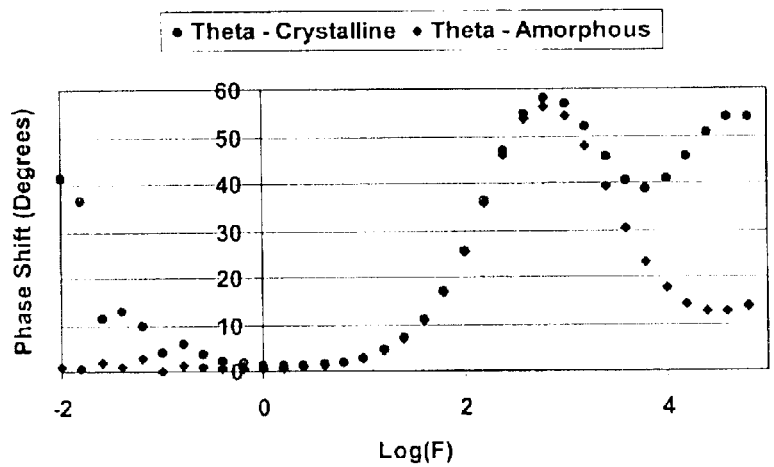
Figure 31C:
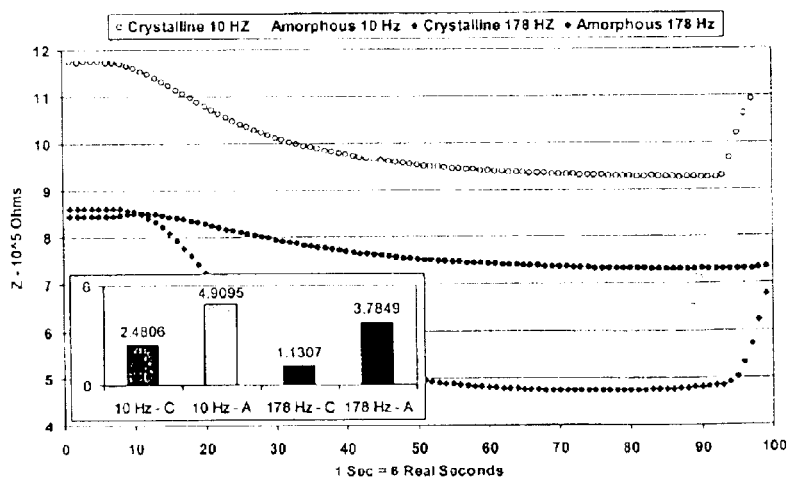

Although only conventional polymers were discussed previously, other polymers may also be used. For example, upon heating of the polymer the thin film changed state to a liquid gel and never returned to a solid. Measurements taken on impedance, and shown in FIGS. 31a to 31c, in the amorphous material shows an increased sensitivity to analyte vapor. This is shown in the larger decrease in impedance at 100% water vapor.

Although only single detectors are used in the examples discussed above, for increased resolving power (ability to differentiate between different gases) a multi polymer array of detectors can also be employed. In such an embodiment, multiple organic sensors, each one more or less sensitive to certain classes of analyte vapors, can be linked together. The response data of each individual sensor is correlated to the rest, providing a larger and more diverse data set. When this data set is compared to previously measured data from known gases, the identity and concentration of the gas tested can be ascertained.

A polymer detector array can be built and the data analyzed and plotted in a 3-D principle component space, characteristic cluster regions formed for each individual gas. These separated clusters showed not only chemical identity as before, but a point along the length of the cluster showed the concentration of vapor present. These long clusters can act as an effective 'fingerprint' for each gas. Fingerprint data acquired for an unknown gas can be compared to the fingerprints of gases already stored in search of an identity and concentration match. Increased number of sensors will result in increased resolving power of the system. In another exemplary embodiment in which an array of hybrid sensors is used, the sensing material substrate may be coated with a single coating of a continuous sensing material and multiple sensors may be placed into contact with the sensing material in order to provide multiple readings and a more accurate determination of the analyte or analytes being detected.

Inventors have devised a hybrid sensor that can accurately and consistently discern between varying concentrations of different organic analytes. This is achieved through the simultaneous measurement and comparison of thickness changes and impedance chances in thin films of a sensing material. The sensor is sensitive to a analytes with different solubility parameters. The use of both thickness and impedance change correlated together has resulted in an increased level of analyte differentiation. Using the mathematical models and knowing the thickness and impedance response at two different concentrations of analyte vapor, the identity and current concentration of organic analyte vapor present can be simultaneously identified.

It is emphasized at this point that the present invention is not intended to be limited to the exemplary embodiments shown and described above. Rather, the present invention is intended to cover the method and apparatus which the includes the use of a hybrid sensor which measures impedance and thickness change of a sensing material in the presence of a particular analyte or analytes sought to be detected.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A hybrid sensor for detecting at least one analyte comprising:
   a sensing material having at least volumetric and impedance responses to the presence of at least one analyte;
   at least one detector in electrical and physical contact with said sensing material for measuring the volumetric and impedance responses of the sensing material; and
   an analyzer for correlating said volumetric and impedance responses into a single measurement to determine at least the identity of the at least one analyte.

2. The hybrid sensor as in claim 1, wherein said analyzer also determines the concentration of the at least one analyte.

3. The hybrid sensor as in claim 1, wherein said detector includes an signal analyzer for facilitating measurement of the impedance of said sensing material.

4. The hybrid sensor as in claim 1, wherein said detector includes a frequency analyzer for measuring the impedance of said sensing material.

5. The hybrid sensor as in claim 4, wherein the frequency analyzer detects the impedance by application of an alternating current to the sensing material.

6. The hybrid sensor as in claim 1, wherein the detector includes a microcantilever sensor having a deflectable arm which deflects in response to a change in the thickness of the sensing material.

7. The hybrid sensor as in claim 6, wherein the deflectable arm includes at least one measurable physical property which changes when said arm deflects and said detector is further capable of measuring a change in said at least one measurable physical property.

8. The hybrid sensor as in claim 6, in which said detector includes a transducer capable of transducing said deflection of said deflectable arm to a measurable electrical signal.

9. The hybrid sensor as in claim 6, in which said deflectable arm includes a piezoresistive member formed one of therein and thereon and said detector includes an electrical circuit capable of measuring a change in resistance of said piezoresistive member due to said deflection.

10. The hybrid sensor as in claim 9, wherein said piezoresistive member comprises barium titanate.

11. The hybrid sensor as in claim 1, in which said sensing material is disposed on a further substrate.

12. The hybrid sensor as in claim 6, wherein said sensing material is formed on a surface and said deflectable arm is in physical contact with said sensing material and disposed essentially parallel to said surface when in rest position.

13. The hybrid sensor as in claim 1, wherein said sensing material comprises a chemical sensor formed of a polymer which undergoes an impedance and volumetric change upon exposure to said at least one analyte.

14. The hybrid sensor as in claim 1, wherein the sensing material comprises a biological sensor formed of either layered biological molecules or composite materials containing biological molecules, the biological sensor being capable of adsorbing said at least one analyte and volumetrically and electrically changing as a result of said adsorption.

15. The hybrid sensor as in claim 14, in which said biological sensor comprises antibodies.

16. The hybrid sensor as in claim 14, in which said biological sensor comprises a functionalized DNA strand disposed on a substrate.

17. The hybrid sensor as in claim 16, in which said at least one analyte comprises the complementary DNA strand of double-stranded DNA.

18. The hybrid sensor as in claim 1, wherein said sensing material comprises at least one polymer matrix material selected from the group consisting of polyvinyl acetate (PVA), polyisobutylene (PIB), polyethylene vinyl acetate (PEVA), poly(4-vinylphenol), poly(styrene-co-allyl alcohol), poly(methylstyrene), poly(N-vinylpyrrolidone), poly(styrene), poly(sulfone), poly(methyl methacrylate), and poly(ethylene oxide).

19. The hybrid sensor as in claim 1, wherein said sensing material comprises at least one analyte sensitive dopant selected from the group consisting nickel acetate, Pd, Pt, and lithium perchlorate.

20. The hybrid sensor as in claim 1, in which said sensing material comprises a discrete deposit of material formed on a surface.

21. The hybrid sensor as in claim 6, in which said deflectable arm includes silicon nitride as a component thereof.

22. The hybrid sensor as in claim 1, in which said at least one analyte is included within one of a gaseous medium and a liquid medium.

23. The hybrid sensor as in claim 6, in which said deflectable arm includes a thickness ranging from 10 microns to 50 microns, a width ranging from 25 microns to 75 microns, and a length ranging from 100 microns to 200 microns.

24. The hybrid sensor as in claim 6, in which said detector is capable of measuring the extent of said deflection of said deflectable arm.

25. The hybrid sensor as in claim 1, wherein the detector measures the impedance of the sensing material at a frequency between 0.01 Hz and 65 kHz.

26. The hybrid sensor as in claim 1, wherein the detector measures the impedance of the sensing material at a frequency between 10 Hz and 178 Hz.

27. The hybrid sensor as in claim 1, wherein the detector measures the impedance of the sensing material at a voltage of between about 0.01 and 0.1 V.

28. The hybrid sensor as in claim 1, wherein the analyte is a volatile organic material.

29. An array of hybrid sensors for detecting analytes, comprising:
   a plurality of discrete sensing materials formed on a surface, each sensing material undergoing a change in impedance and volume in the presence of at least one analyte;
   a corresponding plurality of detectors each individual detector in electrical and physical contact with at least one of said discrete sensing materials for measuring the volumetric and impedance responses of the at least one discrete sensing material; and an analyzer for correlating said volumetric and impedance responses into a single measurement to determine at least the identity of the at least one analyte.

30. The array of hybrid sensors as in claim 29, wherein each sensing material is different from the other sensing materials.

31. The array of hybrid sensors as in claim 29, in which said analyzer further determines the concentration of each of the analytes.

32. The array of hybrid sensors as in claim 29, wherein each sensing material undergoes a volumetric change in response to the presence of a different analyte.

33. The array of hybrid sensors as in claim 29, in which each of the detectors includes a microcantilever sensor including a deflectable arm, the deflectable arm being in physical contact with the sensing material.

34. The array of hybrid sensors as in claim 33, in which each of the microcantilever sensors includes a piezoresistive element in contact with said deflectable arm.

35. The array of hybrid sensors as in claim 34, in which each said piezoresistive element undergoes a change in resistance as a result of the deflection of the deflectable arm due to the volumetric change in said corresponding sensing material, each detector further including an electrical circuit for measuring the resistance of the piezoresistive element.

36. The array of hybrid sensors as in claim 33, in which each said deflectable arm includes at least one measurable physical property which changes when said arm deflects and said detector being capable of measuring the change in said at least one measurable physical property of each deflectable arm.

37. The array of hybrid sensors as in claim 29, in which each said deflectable arm responds measurably differently to a different analyte.

38. A method for detecting an analyte within a medium, comprising:
forming a sensing material which undergoes at least a volumetric and impedance response in the presence of said analyte;
providing at least one detector in electrical and physical contact with said sensing material for measuring the volumetric and impedance responses of the sensing material;
introducing a medium containing said analyte to said sensing material, said medium being one of a liquid and a vapor;
measuring said volumetric and impedance responses with said at least one detector; and
correlating said volumetric and impedance responses into a single measurement to determine at least the identity of the at least one analyte.

39. The method as in claim 38, wherein said detector includes a deflectable microcantilever arm in physical contact with said sensing material the deflectable microcantilever arm having at least one measurable physical property which changes when said microcantilever arm deflects; and
wherein said measuring said volumetric response comprises measuring a change in said at least one measurable physical property.

40. The method as in claim 39, wherein said microcantilever arm includes a piezoresistive member one of therein and thereon, and said measuring comprises measuring a resistance change of said piezoresistive member as a result of one of said deflection.

41. The method as in claim 39, in which said microcantilever arm includes two conductive leads coupled to said piezoresistive member and said measuring includes measuring resistance across said two conductive leads.

42. The method as in claim 38, in which said measuring includes measuring resistance of said sensing material to determine the impedance change of said sensing material each of before and after said step of introducing.

43. The method as in claim 38, wherein said detector includes a signal analyzer in signal communication with said sensing material for measuring the impedance of said sensing material.

44. The method as in claim 38, wherein the analyzing includes determining the concentration of the analyte.

* * * * *